US010934556B2

(12) United States Patent
Sawant et al.

(10) Patent No.: US 10,934,556 B2
(45) Date of Patent: Mar. 2, 2021

(54) REVERSIBLE EXPRESSION SYSTEM FOR TRANSGENE EXPRESSION IN PLANTS

(71) Applicant: Council of Scientific and Industrial Research, New Delhi (IN)

(72) Inventors: Samir Vishwanath Sawant, Lucknow (IN); Surendra Pratap Singh, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 113 days.

(21) Appl. No.: 15/567,040

(22) PCT Filed: Apr. 18, 2016

(86) PCT No.: PCT/IN2016/050113
§ 371 (c)(1),
(2) Date: Oct. 16, 2017

(87) PCT Pub. No.: WO2016/166776
PCT Pub. Date: Oct. 20, 2016

(65) Prior Publication Data
US 2020/0010841 A1 Jan. 9, 2020

(30) Foreign Application Priority Data
Apr. 16, 2015 (IN) .......................... 1060/DEL/2015

(51) Int. Cl.
*C12N 15/82* (2006.01)
(52) U.S. Cl.
CPC ..... *C12N 15/8231* (2013.01); *C12N 15/8289* (2013.01)
(58) Field of Classification Search
CPC ................................................ C12N 15/8231
See application file for complete search history.

(56) References Cited

U.S. PATENT DOCUMENTS

| | | | |
|---|---|---|---|
| 5,955,653 A | 9/1999 | Scott et al. | |
| 7,230,168 B2 | 6/2007 | Huang et al. | |
| 8,361,929 B2 | 1/2013 | Higashitani et al. | |
| 2002/0166140 A1 | 11/2002 | Hamada et al. | |
| 2014/0351999 A1 | 11/2014 | Lutfiyya | |

FOREIGN PATENT DOCUMENTS

| | | |
|---|---|---|
| EP | 0344029 A1 | 11/1989 |
| EP | 2394513 A1 | 12/2011 |
| WO | WO-89/10396 A1 | 11/1989 |
| WO | WO-96/26283 A1 | 8/1996 |
| WO | WO-99/04023 A1 | 1/1999 |

OTHER PUBLICATIONS

Singh, S. et al., Scientific Reports, 5:11274 published online, Jun. 15, 2015; www.nature.com/scientificreports pp. 1-14. (Year: 2015).*
Singh, S. et al., Scientific Reports, published online Jun. 15, 2015; www.nature.com/scientificreports. (Year: 2015).*
Yi, C. et al. Trends in Cell Biology (Nov. 2005), vol. 15, No. 11; pp. 618-615. (Year: 2005).*
Sudhir, S. et al. Plant Biotechnology Journal (2010) vol. 8, pp. 10005-1022. (Year: 2010).*
"International Application Serial No. PCT/IN2016/050113, International Preliminary Report on Patentability dated Oct. 26, 2017", 9 pgs.
International Application Serial No. PCT/IN2016/050113, International Search Report dated Aug. 18, 2016, 6 pgs.
"International Application Serial No. PCT/IN2016/050113, Written Opinion dated Aug. 18, 2016", 7 pgs.
Kawanabe, Takahiro, et al., "Abolition of the Tapetum Suicide Program Ruins Microsorogenesis", *Plant and Cell Physiology*, vol. 47, Issue 6, (2006), 784-787.
Konagaya, Ken-Ichi, et al., "Efficient production of genetically engineered, male-sterile *Arabidopsis thaliana* using anther-specific promoters and genes derived from *Brassica oleracea* and *B. rapa*", *Plant Cell Reports*, 27(11), (2008), 1741-1754.
Li, Shaoqing, et al., "Characterization and Use of Male Sterility in Hybrid Rice Breeding", *Journal of Integrative Plant Biology*, 49(6), (2007), 791-804.
Li, Song Feng, et al., "Suppression and restoration of male fertility using a transcription factor", *Plant Biotechnology Journal*, 5, (2007), 297-312.
Mariani, Celestina, et al., "Induction of male sterility in plants by a chimaeric ribonuclease gene", *Nature*, 347(6295), (1990), 737-741.
Ribarits, Alexandra, et al., "Combination of reversible male sterility and doubled haploid production by targeted inactivation of cytoplasmic glutamine synthetase in developing anthers and pollen", *Plant Biotechnology Journal*, 5(4), (Jul. 2007), 483-494.
Shull, George H., "Chapter 2—Beginnings of the Heterosis Concept", In: *Heterosis*, Gowen, John W., Editor, Iowa State College Press, Ames, IA, (1952), 14-48.
Singh, Sudhir P., "BECLIN1 from *Arabidopsis thaliana* under the generic control of regulated expression systems, a strategy for developing male sterile plants", *Plant Biotechnology Journal*, 8(9), (2010), 1005-1022.

(Continued)

*Primary Examiner* — Russell Kallis
(74) *Attorney, Agent, or Firm* — Schwegman Lundberg & Woessner, P.A.

(57) ABSTRACT

The present invention relates to the development of expression cassettes to achieve tapetum specific reversible expression of transgene in female heterotic parent and in F1 progeny in the plants. The expression cassettes are based on the transcription regulation and light signaling. It includes two vector construct; female expression construct and male regulatory construct. The female expression construct was used to achieve tapetum specific expression of reporter gene while when cross is made with male plants having regulatory cassette, F1 plants were formed with abolished expression of reporter gene. Further, the system was deployed to achieve complete male sterility using candidate gene of male sterility; BECLIN1/ATG6 and successfully restoring the fertility of F1 by crossing with pollen of male regulatory transgenic. Here, we claim the expression system using which reversible male sterility can be achieved by expressing candidate gene for male sterility like BECLIN1 or other.

28 Claims, 5 Drawing Sheets
Specification includes a Sequence Listing.

(56) References Cited

OTHER PUBLICATIONS

Singh, Suman B., et al., "Male Sterility in Cotton", *CICR Technical Bulletin No. 24*, (2012), 1-16.
Singh, Surendra P., et al., "A novel male sterility-fertility restoration system in plants for hybrid seed production", *Scientific Report*, 5, Article No. 11274, (2015), 14 pages.
Takada, Keita, et al., "Expression of a mutated melon ethylene receptor gene Cm-ETR1/H69A affects stamen development in *Nicotiana tabacum*", *Plant Science*, 169(5), (2005), 935-942.
Tester, Mark, et al., "Breeding Technologies to Increase Crop Production in a Changing World", *Science*, 327(5967), (2010), 818-822.
Tsihlis, N. D., et al., "Comparison of Kinetic Parameters of TATA-binding protein and the altered specificity mutant TBPm3", *The FASEB Journal, Experminental Biology 2002: Meeting Abstracts, Part I*, (2002), p. A531.
Yang, Jianping, "Light Regulates COP1-Mediated Degradation of HFR1, a Transcription Factor Essential for Light Signaling in *Arabidopsis*", *The Plant Cell*, 17(3), (2005), 804-821.
Zirkle, Conway, "Chapter 1—Early Ideas on Inbreeding and Crossbreeding", *In: Heterosis*, Gowen, John W., Editor, Iowa State College Press, Ames, (1952), 1-13.

\* cited by examiner

[A] Construct 1 - *Expression module (em)*

[Cloned in pBI101]

[B] Construct 2 - *Male sterility module (ms)*

[Cloned in pBI101]

[C] Construct 2 - *Restoration module (rs)*

[Cloned in modified pCAMBIA1300]

Figure 2B-C

REVERSIBLE EXPRESSION SYSTEM FOR TRANSGENE EXPRESSION IN PLANTS

PRIORITY CLAIM TO RELATED APPLICATIONS

This application is a U.S. national stage application filed under 35 U.S.C. § 371 from International Application Serial No. PCT/IN2016/050113, which was filed 18 Apr. 2016, and published as WO2016/166776 on 20 Oct. 2016, and which claims priority to India Application No. 1060/DEL/2015, filed 16 Apr. 2015, which applications and publication are incorporated by reference as if reproduced herein and made a part hereof in their entirety, and the benefit of priority of each of which is claimed herein.

FIELD OF INVENTION

The present invention relates to an expression system for high level and stringent expression of a transgene in plants and also it's abolished expression in their F1 hybrid generated. Aiming several applications, the method can also be deployed to generate complete male sterile plants using one of the several candidate genes for male sterility and successfully restoring fertility of F1 hybrid, which is requisite for hybrid development.

BACKGROUND OF THE INVENTION AND PRIOR ART

Hybrid vigor, or heterosis, refers to the phenomenon in which the progeny derived from a cross of two inbred lines outperform the parent lines. For example, hybrid crops can produce 15-50% higher yields than inbred varieties (Tester M, Langridge P. (2010) Breeding technologies to increase crop production in a changing world. Science 327:818-22). The utilization of heterosis has produced tremendous economic benefits in worldwide crop production. More than half of the production of major crops such as maize, rice, sorghum, rapeseed, and sunflower comes from hybrid varieties (Li S, Yang D, Zhu Y. 2007. Characterization and use of male sterility in hybrid rice breeding. J. Integr. Plant Biol. 49:791-804). Thus, hybrid breeding contributes significantly to the food supply in the world.

The manifestation of heterosis are increase yield, reproductive ability, size, better quality, resistance to disease and pests, greater adaptability. Hybrid plants have become increasingly important in various commercial food crops around the world. The development of hybrid crops has been one of the major factors behind a dramatic increase in global crop yields. Such improvement is achieved through the selective and controlled breeding of two inbred parent lines, which upon crossing delivers heterosis, or 'hybrid vigour'. This boost in performance, combining the best yield, quality and agronomic characters from each parent, is the result of hybrid breeding.

The hybrid vigor conceptualized (Zirkle C. (1952) Early ideas on inbreeding and crossbreeding, in: Gowen J. W. (Ed.), Heterosis, Iowa State College Press, Ames, pp. 1-13) while Charles Darwin (1876), who was the first scientist to examine the phenomenon in a systematic manner (Darwin C. (1876) The effects of cross and self fertilization in the vegetable kingdom, Murray, London), W. J. Beal in maize (Beal W. J. (1880) Indian corn, Rept Michigan State Board. Agr. 19, 279-289.), Shull in plant breeding (Shull G. H. (1952) Beginnings of the heterosis concept, in: Gowen J. W. (Ed.), Heterosis, Iowa State College Press, Ames, pp. 14-48) observed. Corn was the first hybrid seed crop to be marketed extensively, and it is still the most important economic crop grown in the U.S. The most successful breeding efforts of $20^{th}$ century are production of hybrid varieties of maize in US (six-fold increase between 1930-to-1990), cotton in India and rice in China.

Producing hybrid seeds of self-pollinating plants requires emasculation; the removal of functional pollen grains to prevent self-pollination. Before the mid-twentieth century, emasculation in hybrid seed production involved manual labour, machines, or chemical treatments and thus was costly, inefficient, and even damaging to the environment.

Another method is the induction of male sterility. Male sterility refers to the failure to produce dehiscent anthers, functional pollen, and viable male gametes. Male sterility was first observed by the German botanist Joseph Gottlieb K'olreuter in (1763), male sterility has been reported in more than 610 plant species (Kaul MLH. 1988. Male Sterility in Higher Plants. New York: Springer-Verlag). The use of male sterility (MS) reduces the cost of hybrid seed by eliminating the process of emasculation, also has several advantage over conventional breeding methods. There are three main types of male sterility observed in nature. All three types of male sterility are used in commercial breeding programs to ensure cross-pollination to produce hybrid seeds in different crops; a) Genetic male sterility (GMS), a) Cytoplasmic male sterility (CMS) and c) Cytoplasmic genetic male sterility (CGMS).

In genetic male sterility (GMS), pollen sterility is caused by nuclear gene alone. The use of GSM is limited as, (i) GMS is less stable. Sometimes, sterile plants become fertile under low temperature conditions. (ii) In GMS, the lines segregate into male sterile and fertile plants in 1:1 ratio. (iii) Conversion of a genotype into GMS needs selfing after each backcross to isolate recessive genes and hence more number of generations is required. (iv) It requires more area as 50% of the population is fertile. (v) The quantity of seed produced is less. (vi) There is possibility of admixture if fertile plants are not properly rogued out (Singh Suman Bala, Singh Phundan, Mayee C D (2012) MALE STERILITY IN COTTON. CICR technical bulletin no: 24). For the production of the hybrid seed, complete restoration of fertility is required which is constrain in using GMS, also broader crop applicability is also a limitation, although, environment-sensitive GMS (EGMS) systems are also reported in some crops.

Cytoplasmic male sterility (CMS), which is caused by mitochondrial genes with coupled nuclear genes, manifestation of male sterility in these may be both entirely controlled by cytoplamsic factors (cytoplasmic) or by the interaction between cytoplasmic and nuclear factors. They follow cytoplasmic inheritance (non-mendelian inheritance). Here the sterility is transmitted only through the female and all progeny will be sterile. This is applicable to those crops where the economic product is other than seed (vegetative part). It lack restoration of F1, therefore a separate parent (maintainer line) is required for the propagation.

When nuclear genes for fertility restoration (Rf) are available for CMS system in any crop, it is called as cytoplasmic genetic male sterility (CGMS). This type of male sterility has provision for restoration of fertility, which is not possible in cytoplasmic male sterility. The fertility is restored by the Rf gene (s) present in the nucleus. Thus, the combination of both nuclear genes and cytoplasmic factors determines the fertility or sterility in such plants. The use of this system has limitations like, a) In CGMS, only limited number of crosses can be made due to availability of limited number of restorers. b) CMS is solely controlled by cytoplasmic genes and hence it may have some adverse effect on other characters. c) It is not possible to breed a variety from CMS line.

The use of genetic engineering in inducing male sterility is called transgenic male sterility. The first transgenic system was described by Mariani, 1990 (Mariani C., Beuckleer D, Truettner J, Leemans J and Goldberg R B (1990) Nature, 347, 737-741). The male gametophytic (microspore) or sporophytic (microspore mother cell (MMC), tapetum, middle layer, stomium cell) tissue were targeted which ablation resulted male sterility. Of the said tissue male sporophytic tissue tapetum ablation and impaired degeneration was targeted by several worker to achieve male sterility. Tapetum is innermost wall layer of male reproductive organ anther. Tapetum synthesise pollen wall material, enzymes, nutrients, secondary metabolites etc. and deliver to the developing microspores. When pollen tetrad form as result of meiosis in MMC the tetrad is surrounded in callose matrix, tapetum releases calase enzyme which is degrade callose and microspores releases from callose matrix. Post meiotic tapetum undergo PCD like degeneration to release nutrients, callase enzyme, pollen wall material which are important for pollen viability. It is reported that alteration in the tapetal PCD either early or delayed resulted pollen abortion and male sterility.

The genes that are used to generate male sterile plants by interfering tapetal degeneration are: BARNASE (RNase) (Mariani et al., 1990; Block and Debrouwer 1993; Roberts et al., 1995; Zhan et al., 1996; Block et al., 1997; Jagannath et al., 2001; Luo et al., 2006; Roque et al., 2007; Cao et al., 2008; Liu and Liu, 2008; Garcia-Sogo et al., 2010), RNase T-I (Mariani et al., 1990; Denis et al., 1993), *Mammalian uncoupling protein* (George et al., 1990), *Diptheria toxin A-chain* (Koltunow et al., 1990; Thorsness et al., 1993; Twell, 1995; Lee et al, 2003; Liu and Liu, 2008; Guerineau et al., 2003), BAX (Kawanabe, T., Ariizumi, T., Kawai-Yamada, M., Uchimiya, H. and Toriyama, K. (2006) Abolition of the tapetum suicide program ruins microsporogenesis. Plant Cell Physiol. 47, 784-787), AtBECLIN1 (Sudhir Pratap Singh, Tripti Pandey, Rakesh Srivastav, Praveen C. Verma, Praduman K. Singh, Rakesh Tuli and Samir V. Sawant (2010) BECLIN 1 from *Arabidopsis thaliana* under the generic control of regulated expression systems, a strategy for developing male sterile plants. Plant Biotech. J. 8, 1005-1022).

Tapetum specific expression of melon ethylene receptor genes (ETR1/H69A and ERS1/H70A) delays tapetum generation followed by male sterility (Takada, K., Ishimaru, K., Minamisawa, K., Kamada, H. and Ezura, H (2005a) Expression of a mutated melon ethylene receptor gene Cm-ETR1/H69A affects stamen development in *Nicotiana tabacum*. Plant Sci. 169, 935-942). An apoptotic protein inhibitor was identified in *Arabidopsis*, Bax Inhibitor-1. Kawanabe et al. (2006) showed that expression of *Arabidopsis* Bax Inhibitor-1 (AtBI-1) in tapetum inhibited its degeneration, by blocking cell death pathway, and subsequently resulted pollen abortion (Kawanabe, T., Ariizumi, T., Kawai-Yamada, M., Uchimiya, H. and Toriyama, K. (2006) Abolition of the Tapetum Suicide Program Ruins Microsporogenesis. Plant Cell Physiol. 47(6), 784-787). Cysteine proteases from *Brassica*, BoCysP1 and BoCP3, have been identified as candidate genes for male sterility. These proteins found to inhibit programmed cell death of tapetum (Konagaya, K., Ando, S., Kamachi, S., Tsuda, M. and Tabei, Y. (2008) Efficient production of genetically engineered male sterile *Arabidopsis thaliana* using anther-specific promoters and genes derived from *Brassica oleracea* and *B. rapa*. Plant Cell Rep. 27(11), 1741-1754).

For the production of hybrid seed the major challenge is the restoration of the fertility of the F1 hybrid to develop seeds. While using the transgenic male sterility, it has several advantages but for the successful production of hybrid seed it is pre-requisite to have efficient restoration of the fertility of F1 hybrid. The reversible male sterility was achieved by expressing cytokinin oxidase (Huang, et al. (2007) Reversible male sterility in transgenic plants by expression of cytokinin oxidase. U.S. Pat. No. 7,230,168), AtMYB103 (Li, S F, Iacuone, S and Parish, R W (2007) Suppression and restoration of male fertility using a transcription factor, Plant Biotechnology Journal, 5, 297-312), glutamine synthetase (Ribarits, A, Mamun, ANK, Li, S, Resch, T, Fiers, M, Heberle-Bors, E, Liu, C and Touraev, A (2007) Combination of reversible male sterility and doubled haploid production by targeted inactivation of cytoplasmic glutamine synthetase in developing anthers and pollen. Plant Biotechnology Journal, 5, 483-494). Some male sterility and restoration systems are: Patent EP344029 and WO89/10396 described a system for producing a male sterile plant by transforming a plant with a DNA encoding barnase under the control of a tapetum-specific promoter resulted male sterility (Mariani et al., 1990) and also in other (Hird et. al., 1993; Paul et. al., 1992). PCT International Publication WO96/26283 refers that it causes problem unfavourable characteristics in rice. It is also reported that similar phenomena are observed not only in rice but in lettuce (Reymaerts et. al., 1993). Patent Application 20020166140 used mutant barnase to avoid disadvantageous effects. WO 99/04023 proposed a method of resulting male sterility of plants by the use of DNA molecule that encode avidin, Fertility can be restored by spraying the plant with a solution of biotin. U.S. Pat. No. 7,230,168 described transformation of a plant cell with a nucleic acid construct encoding cytokinin oxidase causes male sterility. Fertility can be achieved by spray of cytokinin oxidase 1 inhibitor. EP2394513A1 and U.S. Pat. No. 8,361,929B2 describe low temperature and high temperature sensitive male sterility in gramineous plant and fertility restoration by Auxin spray.

LIMITATIONS OF PRIOR ART

The above reported systems of the male sterility inducing method and their restoration to ensure the hybrid seed production has following limitation:

Lack of efficient system to achieve high level and stringent expression of the candidate gene for male sterility. The expression of such gene that has dominant negative effect may have more than one stringency control to avoid their leaky expressions which has negative effect on plants.

Stringent system with high level of candidate gene expression is needed to achieve the complete male sterility.

Efficient restoration of the fertility of F1 hybrid required where expression of candidate gene for male sterility can be abolished at transcription level.

The system has broad crop applicability.

The system which can be used in intra as well as inter-specific hybrids production.

Objectives of the Present Invention

Main objective of the present invention is to have transgenic with tightly regulated reversible expression of desired genes.

Another objective of the invention is to develop an expression system which can effectively express desired gene in transgenic.

One of the objectives of the invention is to have an expression system with tapetum specific expression of desired gene.

Another objective is to use TA29 as one of the many promoters used to express the gene specific to tapetum.

Yet another objective is to make tapetum specific expression by TA29 more stringent and high level by regulating it through another regulatory component.

Still another objective to develop regulatory component with a constitutive promoter expressing regulatory protein conjugate that regulate expression component.

Still another objectives of the invention is to have an expression system (ES) with both component, tapetum specific promoter (more specific TA29 with modification):reporter gene:transcription terminator with polyadenylation sequences:constitutive promoter:Nuclear transcription factor (which may be Hfr1) with TATA binding protein (TBP): transcription terminator with polyadenylation sequences.

One more objective is to express a gene that impairs tapetal degeneration; one may be BECLIN1 place of reporter gene as described in objective 7, to achieve male sterility (MS system).

Yet another objective is to have restoration system (RS) which express restorer protein specific to tapetum using suitable tapetum specific promoter which express restorer protein.

Yet another objective is to transform desired variety of plant with expression (ES) vector.

Yet another objective is to transform desired variety of plant with expression (RS) vector.

Still another objective is to cross female ES transgenic plants with male RS plants to generate F1 and observe expression of reporter gene.

One more objective is to transform desired variety of plant with expression (MS) vector and observe degree of pollen abortion (male sterility).

Yet another objective is to cross female MS transgenic plants with male RS plants to generate F1 and observe restoration of fertility of F1 hybrids.

SUMMARY OF THE INVENTION

In an aspect of the present disclosure, there is provided a MS DNA construct comprising: (a) a first expression cassette comprising a first tissue specific promoter operably linked to a desired gene of interest, expression of which leads to male sterility in plants, and a terminator; and (b) a second regulatory cassette comprising a second promoter operably linked to a fragment encoding a fusion peptide of N-terminal fragment of a transcription factor and TBPm3 having SEQ ID NO: 6, and a terminator.

In an aspect of the present disclosure, there is provided a ES DNA construct comprising: (a) a first expression cassette comprising a first tissue specific promoter operably linked to a gene of interest, and a terminator; and (b) a second regulatory cassette comprising a second promoter operably linked to a fragment encoding a fusion peptide of N-terminal fragment of a transcription factor and TBPm3 having SEQ ID NO: 6, and a terminator.

In an aspect of the present disclosure, there is provided a RS DNA construct comprising a third issue specific promoter operably linked to a restorer gene, and a terminator.

In an aspect of the present disclosure, there is provided a reversible expression system for modulating male sterility in plants, said system comprising: (a) a first component consisting of: (i) a first expression cassette comprising: a first tissue specific promoter operably linked to a desired gene of interest, expression of which causes male sterility in plants, and a terminator; and (ii) a second regulatory cassette comprising: a second promoter operably linked to a fragment encoding a fusion peptide of N-terminal fragment of a transcription factor and TBPm3 having SEQ ID NO: 6, and a terminator; (b) a second component consisting of an expression cassette comprising: a third tissue specific promoter operably linked to a restorer gene, and a terminator.

In an aspect of the present disclosure, there is provided a reversible expression system for modulating transgene expression in plants, said system comprising: (a) a first component consisting of: (i) a first expression cassette comprising: a first tissue specific promoter operably linked to a gene of interest, and a terminator; and (ii) a second regulatory cassette comprising: a second promoter operably linked to a fragment encoding a fusion peptide of N-terminal fragment of a transcription factor and TBPm3 having SEQ ID NO: 6, and a terminator; (b) a second component consisting of an expression cassette comprising: a third tissue specific promoter operably linked to a restorer gene, and a terminator.

In an aspect of the present disclosure, there is provided a DNA vector comprising a MS DNA construct comprising: (a) a first expression cassette comprising a first tissue specific promoter operably linked to a desired gene of interest, expression of which leads to male sterility in plants, and a terminator; and (b) a second regulatory cassette comprising a second promoter operably linked to a fragment encoding a fusion peptide of N-terminal fragment of a transcription factor and TBPm3 having SEQ ID NO: 6, and a terminator.

In an aspect of the present disclosure, there is provided a DNA vector comprising a ES DNA construct comprising: (a) a first expression cassette comprising a first tissue specific promoter operably linked to a gene of interest, and a terminator; and (b) a second regulatory cassette comprising a second promoter operably linked to a fragment encoding a fusion peptide of N-terminal fragment of a transcription factor and TBPm3 having SEQ ID NO: 6, and a terminator.

In an aspect of the present disclosure, there is provided a DNA vector comprising a RS DNA construct comprising a third issue specific promoter operably linked to a restorer gene, and a terminator.

In an aspect of the present disclosure, there is provided a recombinant host cell comprising a MS DNA construct comprising: (a) a first expression cassette comprising a first tissue specific promoter operably linked to a desired gene of interest, expression of which leads to male sterility in plants, and a terminator; and (b) a second regulatory cassette comprising a second promoter operably linked to a fragment encoding a fusion peptide of N-terminal fragment of a transcription factor and TBPm3 having SEQ ID NO: 6, and a terminator.

In an aspect of the present disclosure, there is provided a recombinant host cell comprising a ES DNA construct comprising: (a) a first expression cassette comprising a first tissue specific promoter operably linked to a gene of interest, and a terminator; and (b) a second regulatory cassette comprising a second promoter operably linked to a fragment encoding a fusion peptide of N-terminal fragment of a transcription factor and TBPm3 having SEQ ID NO: 6, and a terminator.

In an aspect of the present disclosure, there is provided a recombinant host cell comprising a RS DNA construct comprising a third issue specific promoter operably linked to a restorer gene, and a terminator.

In an aspect of the present disclosure, there is provided a recombinant host cell comprising a DNA vector, said DNA vector comprising a MS DNA construct comprising: (a) a first expression cassette comprising a first tissue specific promoter operably linked to a desired gene of interest, expression of which leads to male sterility in plants, and a terminator; and (b) a second regulatory cassette comprising a second promoter operably linked to a fragment encoding a fusion peptide of N-terminal fragment of a transcription factor and TBPm3 having SEQ ID NO: 6, and a terminator.

In an aspect of the present disclosure, there is provided a recombinant host cell comprising a DNA vector, said DNA vector comprising a ES DNA construct comprising: (a) a first expression cassette comprising a first tissue specific promoter operably linked to a gene of interest, and a terminator; and (b) a second regulatory cassette comprising a second promoter operably linked to a fragment encoding a fusion peptide of N-terminal fragment of a transcription factor and TBPm3 having SEQ ID NO: 6, and a terminator.

In an aspect of the present disclosure, there is provided a recombinant host cell comprising a DNA vector, said DNA vector comprising a RS DNA construct comprising a third issue specific promoter operably linked to a restorer gene, and a terminator.

In an aspect of the present disclosure, there is provided a transgenic plant or parts thereof, including seeds comprising a MS DNA construct comprising: (a) a first expression cassette comprising a first tissue specific promoter operably linked to a desired gene of interest, expression of which leads to male sterility in plants, and a terminator; and (b) a second regulatory cassette comprising a second promoter operably linked to a fragment encoding a fusion peptide of N-terminal fragment of a transcription factor and TBPm3 having SEQ ID NO: 6, and a terminator, wherein the transgenic plant is male sterile.

In an aspect of the present disclosure, there is provided a method of obtaining a transgenic plant or parts thereof, including seeds comprising a MS DNA construct comprising: (a) a first expression cassette comprising a first tissue specific promoter operably linked to a desired gene of interest, expression of which leads to male sterility in plants, and a terminator; and (b) a second regulatory cassette comprising a second promoter operably linked to a fragment encoding a fusion peptide of N-terminal fragment of a transcription factor and TBPm3 having SEQ ID NO: 6, and a terminator, wherein the transgenic plant is male sterile, said method comprising: (a) obtaining a MS DNA construct comprising: (i) a first expression cassette comprising a first tissue specific promoter operably linked to a desired gene of interest, expression of which leads to male sterility in plants, and a terminator; and (ii) a second regulatory cassette comprising a second promoter operably linked to a fragment encoding a fusion peptide of N-terminal fragment of a transcription factor and TBPm3 having SEQ ID NO: 6, and a terminator; or (b) obtaining a recombinant host cell comprising said MS DNA construct; (c) transforming plant cells with said MS DNA construct or said recombinant host cells to obtain transformed cells; and (d) selecting and regenerating transformed cells to obtain said transgenic plants or parts thereof, including seeds, wherein said transgenic plant is male sterile.

In an aspect of the present disclosure, there is provided a transgenic plant or parts thereof, including seeds comprising a RS DNA construct comprising a third issue specific promoter operably linked to a restorer gene, and a terminator, wherein said transgenic plant is capable of restoring male sterility.

In an aspect of the present disclosure, there is provided a method of obtaining a transgenic plant or parts thereof, including seeds comprising a RS DNA construct comprising a third issue specific promoter operably linked to a restorer gene, and a terminator, wherein said transgenic plant is capable of restoring male sterility, said method comprising: (a) obtaining a RS DNA construct comprising a third issue specific promoter operably linked to a restorer gene, and a terminator; or (b) obtaining a recombinant host cell comprising said RS DNA construct; (c) transforming plant cells with said RS DNA construct or said recombinant host cells to obtain transformed cells; and (d) selecting and regenerating transformed cells to obtain said transgenic plants or parts thereof, including seeds, wherein said transgenic plant is capable of restoring male sterility.

In an aspect of the present disclosure, there is provided a hybrid plant or parts thereof, including seeds comprising a MS DNA construct and RS DNA construct, said MS DNA construct comprising: (i) a first expression cassette comprising a first tissue specific promoter operably linked to a desired gene of interest, expression of which leads to male sterility in plants, and a terminator; and (ii) a second regulatory cassette comprising a second promoter operably linked to a fragment encoding a fusion peptide of N-terminal fragment of a transcription factor and TBPm3 having SEQ ID NO: 6, and a terminator; and said RS DNA construct comprising a third issue specific promoter operably linked to a restorer gene, and a terminator.

In an aspect of the present disclosure, there is provided a method of obtaining a hybrid plant or parts thereof, including seeds, comprising a MS DNA construct and RS DNA construct, said method comprising: (a) obtaining a female transgenic plant comprising a MS DNA construct comprising: (i) a first expression cassette comprising a first tissue specific promoter operably linked to a desired gene of interest, expression of which leads to male sterility in plants, and a terminator; and (ii) a second regulatory cassette comprising a second promoter operably linked to a fragment encoding a fusion peptide of N-terminal fragment of a transcription factor and TBPm3 having SEQ ID NO: 6, and a terminator, wherein said plant is male sterile; (b) obtaining a male transgenic plant comprising a third issue specific promoter operably linked to a restorer gene, and a terminator, wherein said plant is capable of restoring male sterility; (c) crossing said female and male plant; (d) obtaining hybrid seeds from said female plant of step (c) which comprises said MS DNA construct and said RS DNA construct, wherein in said plants, male fertility is restored.

In an aspect of the present disclosure, there is provided a transgenic plant or parts thereof, including seeds, comprising a ES DNA construct comprising: (a) a first expression cassette comprising a first tissue specific promoter operably linked to a gene of interest, and a terminator; and (b) a second regulatory cassette comprising a second promoter operably linked to a fragment encoding a fusion peptide of N-terminal fragment of a transcription factor and TBPm3 having SEQ ID NO: 6, and a terminator, wherein said plant is capable of expression of a gene of interest.

In an aspect of the present disclosure, there is provided a method of obtaining a transgenic plant or parts thereof, including seeds comprising a ES DNA construct, said method comprising: (a) obtaining a ES DNA construct comprising: (i) a first expression cassette comprising a first tissue specific promoter operably linked to a gene of interest, and a terminator; and (ii) a second regulatory cassette comprising a second promoter operably linked to a fragment encoding a fusion peptide of N-terminal fragment of a transcription factor and TBPm3 having SEQ ID NO: 6, and a terminator; or (b) obtaining a recombinant host cell comprising said ES DNA construct; (c) transforming plant cells with said ES DNA construct or recombinant host cells to obtain transformed cells; and (d) selecting and regenerating transformed cells to obtain a transgenic plant capable of expressing a gene of interest.

In an aspect of the present disclosure, there is provided a transgenic plant or parts thereof, including seeds comprising a RS DNA construct comprising a third issue specific promoter operably linked to a restorer gene, and a terminator, wherein said plant is capable of inhibiting expression of a gene of interest.

In an aspect of the present disclosure, there is provided a method for obtaining a transgenic plant or parts thereof, including seeds comprising a RS DNA construct, wherein said plant is capable of inhibiting expression of a gene of interest, said method comprising the steps of: (a) obtaining a RS DNA construct comprising a third issue specific promoter operably linked to a restorer gene, and a terminator; or (b) obtaining a recombinant host cell comprising said RS DNA construct; (c) transforming plant cells with said RS DNA construct or recombinant host cells to obtain transformed cells; and (d) selecting and regenerating transformed cells to obtain said transgenic plant capable of inhibiting expression of a gene of interest.

In an aspect of the present disclosure, there is provided a method of switching off expression of a gene of interest in a F1 population of plants or parts thereof, including seeds, said method comprising: (a) obtaining a female transgenic plant comprising ES DNA construct comprising: (i) a first expression cassette comprising a first tissue specific promoter operably linked to a gene of interest, and a terminator; and (ii) a second regulatory cassette comprising a second promoter operably linked to a fragment encoding a fusion peptide of N-terminal fragment of a transcription factor and TBPm3 having SEQ ID NO: 6, and a terminator; (b) obtaining a male transgenic plant comprising a RS DNA construct comprising a third issue specific promoter operably linked to a restorer gene, and a terminator; (c) crossing said female and male plant; (d) obtaining hybrid seeds from said female plant of step (c), wherein said hybrid seeds comprise said ES DNA construct and RS DNA construct and does not express said gene of interest.

In an aspect of the present disclosure, there is provided a MS DNA construct comprising: (a) a first expression cassette comprising a first tissue specific promoter operably linked to a desired gene of interest, expression of which leads to male sterility in plants, and a terminator; and (b) a second regulatory cassette comprising a second promoter operably linked to a fragment encoding a fusion peptide of N-terminal fragment of a transcription factor and TBPm3 having SEQ ID NO: 6, and a terminator, for use in making transgenic plants.

In an aspect of the present disclosure, there is provided a ES DNA construct comprising: (a) a first expression cassette comprising a first tissue specific promoter operably linked to a gene of interest, and a terminator; and (b) a second regulatory cassette comprising a second promoter operably linked to a fragment encoding a fusion peptide of N-terminal fragment of a transcription factor and TBPm3 having SEQ ID NO: 6, and a terminator, for use in making transgenic plants.

In an aspect of the present disclosure, there is provided a RS DNA construct comprising a third issue specific promoter operably linked to a restorer gene, and a terminator, for use in making transgenic plants.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF THE ACCOMPANYING DRAWINGS

The following drawings form part of the present specification and are included to further illustrate aspects of the present disclosure. The disclosure may be better understood by reference to the drawings in combination with the detailed description of the specific embodiments presented herein.

FIG. 1A depicts the vector construct 1 which is expression module (em) contain two expression cassettes; in first tapetum specific promoter with mutated TATA-box to TGTA drives the expression of reporter gene gusA while in second cassette artificial promoter Pcec express conjugated protein $HFRI^{n-131aa}$-TBPm3. The expression module cloned in the binary vector pBI101 with NPTII as selectable marker gene for antibiotic. ($TA_{29(m)}$=Tapetum specific promoter from tobacco with mutated TATA box to TGTA, gusA=reporter gene for β-glucuronidase, Pcec=artificial promoter, $HFRI^{n-131aa}$=N-terminus 131 amino acid fragment of HFR1 that lack it function but retain ability to interact with COP1 protein, TBPm3=TATA binding protein with three amino acid substitution ($Ile_{152}$ to $Phe_{152}$, $Val_{161}$ to $Thr_{161}$, and $Leu_{163}$ to $Val_{163}$), Tnos=transcriptional terminator).

FIG. 1B depicts vector construct 2 which is male sterility module (ms); It is similar to vector construct 1 except the candidate gene of male sterility Arabidopsis BECLIN in place of gusA.

FIG. 1C depicts vector construct 3 which is restoration module (rs); tapetum specific promoter A9 from Arabidopsis express $COP1^{L105A}$ (Constitutive photomorphogenic1) with amino acid mutation Leu to Ala increases nuclear abundance of the protein. The restoration module cloned in binary vector modified pCAMBIA1300 (of Cambia Institute, Canberra, Australia) with hptII as antibiotic marker gene. The vector is modified by replacing CaMV35S promoter by pNOS promoter to avoid leaky expression of COP1 due to bidirectional expression possibility by CaMV35S promoter.

FIG. 2A depicts proposed model to achieve reversible male sterility; ♀-parent should be transformed with MS module which resulted in complete male sterility while ♂-parent with RS module with normal fertility, when both crossed to raise F1 with abolished expression of candidate gene (gusA/BECLIN1).

FIG. 2B depicts male sterility (ms) module consists of two component; expression component and regulatory component. Promoter Pcec direct the expression of $HFR1^{n-131aa}$-TBPm3 conjugated protein which localized to nucleus where it recognize mutated TATA box i.e. TGTA of TA29 promoter and bind to initiate transcriptional pre-initiation formation (PIC) which resulted in the expression of the AtBECLIN1 in the anther tapetum followed by pollen abortion i.e. male sterility.

FIG. 2C depicts restoration module (rs) when transform in the ♂-parent, tapetum specific A9 promoter drives the expression of COP1$^{L105A}$ in the anther tapetum which do not interfere with tapetal degeneration mechanism and plants are remaining fertile.

FIG. 2D depicts the mechanism of fertility restoration of F1 hybrid. When ♀-parent expressing MS module crossed with ♂-parent expressing RS module, F1 hybrid form which contains both ms and rs module expressing in same tapetal cell. Pcec direct the expression of conjugated protein HFR1$^{n-13aa}$-TBPm3 while A9 direct the expression of COP1$^{L105A}$ which localized in the nucleus and physically interact with HFR1$^{n-131aa}$ component and further resulted in sequential degradation of HFR1$^{n-131aa}$-TBPm3. Therefore, it will be not available to initiate the PIC formation on the TA29 mutated TATA box (TGTA), hence, no transcriptional expression of AtBECLIN1 post-meiotically and normal tapetal degeneration resulted fertility restoration of F1 hybrids.

FIG. 3i depicts flour-metric GUS analysis in S2 and S3 anther developmental stages of 10 independent transgenic lines expressing expression module (es) in tobacco with (n=3), expression were normalized with control (NTPH), ES transgenic were showing high expression of gusA protein while when cross is made ES(♀)xRS(♂) to raise F1, abolished expression of gusA protein was found in F1.

FIG. 3ii A-C depicts histochemical GUS analysis; MS transgenic showing expression of gusA protein specific to tapetum of anther in S3 anther developmental stage while in F1 [ES(♀)xRS(♂)] no expression of gusA protein was found.

FIG. 4A depicts the schematic presentation of the hypothesis; the vector construct with MS module will be transformed in female parent showing complete male sterility, while RS module in male parent with normal fertility. When both crossed, F1 hybrid derived with restored fertility.

FIG. 4B depicts Pollen viability (Fluorescein diacetate-Propedium iodide stained pollen, FDA green fluorescence show viable while PI red fluorescence showing abortive pollen), pollen ermination and seed setting in transgenic with ms module, rs module and F1-hybrids [MS(♀)x RS(♂)]. Transgenic with MS module are showing complete male sterility with no seed setting while transgenic with rs module show fertility similar to control, when both crossed [MS(♀)xRS(♂)]. F1 hybrid derived with restored pollen fertility and normal seed setting ♂ similar to control tobacco.

Figure 1:
Figure 1:
Figure 1:
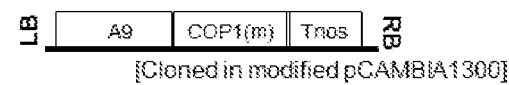

FIG. 6ii depicts the relative expression of COP1$^{L105A}$ in different anther development stages (S1-S6) of RS transgenic, its predominantly express in S1 stage of the anther development. UBIQ was used for normalization, and the error bars indicate the SD of three independent experiments.

FIG. 6iii depicts the relative expression of BECLIN1 and COP1$^{L105A}$ in different anther development stages (S1-S6) of F1 plants [MS(♀)xRS(♂)], COP1$^{L105A}$ expression was found predominantly to S1 while diminished expression of BECLIN1 expression. UBIQ was used for normalization, and the error bars indicate the SD of three independent experiments.

FIG. 6iv depicts the relative expression of BECLIN1 in the S3 developmental stage of ms transgenic and F1 was observed, high level of relative expression of BECLIN1 in the ms transgenic while diminished in F1. UBIQ was used for normalization, and the error bars indicate the SD of three independent experiments.

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively, and any and all combinations of any or more of such steps or features.

In one embodiment of the invention an expression subsystem (ES) constructed which expresses reporter gene gusA in the anther tapetum at post meiotic stage of the anther development. The expression achieved using the ES was stringent and high level, driven by tapetum-specific promoter with two level of control that makes the system highly efficient.

In another embodiment the restoration subsystem (RS) constructed which expresses regulatory protein COP1(m) in the anther tapetum driven by another tapetum-specific promoter at post-meiotic anther but prior to ES.

In yet another embodiment of the invention expression module was transformed in one plant that is used as female-parent in crossing while restoration module in other that is used as male-parent in crossing, transgenic plants were generated and cross was made between female ES and male RS transgenics to generate F1 plants. The expression of reporter protein (gusA) was found high and stringently to post-meiotic tapetum of ES transgenic while in their $F_1$ the expression was completely abolished.

In still another embodiment expression system (ES) was used to express the candidate gene for male sterility that impairs the normal tapetum degeneration. Tapetum is the innermost wall layer of the male reproductive organ anther in flowering plants. Post meiotic PCD like degeneration of tapetum is crucial for pollen fertility. Alteration in the tapetal PCD (early/delayed) resulted in abortive pollen formation. Various genes were used to achieve male sterile transgenic plants by altering the tapetal degeneration; here in present invention we use express Arabidopsis BECLIN1/ATG6 using the expression system (ES), the system is now male sterility (MS) system. The transgenic expressing male sterility (MS) system were completely male sterile as was reported previously.

For the development of the hybrid seed it is pre-requisite to have the sufficient restoration of the fertility of the F1 hybrid. Efficient restoration of fertility of F1 hybrid is limitation in the previous systems.

In still another embodiment of the present invention transgenic plants with male sterility (MS) system which were completely male sterile, were used as female-parent in crossing while transgenic of restoration module (RS) with normal fertility were used as male-parent in crossing [MS (♀)xRS(♂)], to generate $F_1$ plants. Abolished expression of BECLIN1 transcript was found in $F_1$ in post-meiotic anther tapetum, therefore, normal tapetal degeneration occurs which results to restored fertility of $F_1$-hybrid.

The expression vectors claimed in this invention are the good tool to achieve reversible expression of candidate gene or more specifically BECLIN1. The restoration method of male sterility of present invention which is reliable as complete restoration was achieved, broad applicability both in intra- as well as inter-specific hybrids, toxin free as no chemical used, not sensitive to environmental factor like temperature.

In the present invention definitions of the terms are, A "cloning vector" is a DNA molecule, such as a plasmid, cosmid, or bacteriophage that has the capability of replicating autonomously in a host cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide antibiotic or herbicide resistance.

A "reporter gene" is a gene whose phenotypic expression is easy to monitor; used to study promoter activity in different tissues or developmental stages.

A "promoter" is a region of DNA that initiates transcription of a particular gene. Promoters are located near the transcription start sites of genes, on the same strand and upstream on the DNA (towards the 3' region of the anti-sense strand, also called template strand and non-coding strand). Promoters can be about 100-1000 base pairs long.

A "constitutive promoter" is an unregulated promoter that allows for continual transcription of its associated gene.

A "tapetum-specific promoter" is a regulated promoter that allows expression of the gene only to the tapetum tissue of the anther.

The term "expression" refers to the biosynthesis of a gene product. For example, in the case of a structural gene, expression involves transcription of the structural gene into mRNA and the translation of mRNA into one or more polypeptides.

An "expression cassette" is a DNA molecule comprising a gene that is expressed in a host cell and a promoter, driving its expression. Typically, gene expression is placed under the control of certain tissue-specific regulatory elements.

A "transcription factor" is a protein that binds to a cis-regulatory element (eg. an enhancer, a TATA box) and thereby, directly or indirectly, affects the initiation of transcription.

A "recombinant vector" is a vector in which a foreign DNA has been inserted.

An "expression vector" is a vector in which an expression cassette has been genetically engineered.

A "binary vector" is able to replicate in both *E. coli* and *Agrobacterium tumefaciens*. It typically contains a foreign DNA in place of T-DNA, the left and right T-DNA borders, marker for selection and maintenance in both *E. coli* and *Agrobacterium tumefaciens*, a selectable marker for plants. This plasmid is said to be disarmed since its tumor-inducing genes located in the T-DNA have been removed.

A "suitable promoter" includes a tissue-specific or cell-specific promoter that controls gene expression in those particular cells of a particular tissue. An "anther-specific promoter" is a DNA sequence that directs a higher level of transcription of an associated gene in anther tissue than in some or all other tissues of a plant. In present invention suitable promoter directs expression only in cells that are critical for the formation or function of pollen, including tapetum cells, pollen mother cells, and early microspores.

The program cell death (PCD)/apoptosis is a genetically directed process of cell self-destruction that is marked by the fragmentation of nuclear DNA, is activated either by the presence of a stimulus or removal of a suppressing agent or stimulus, and is a normal physiological process eliminating DNA-damaged, superfluous, or unwanted cells called also programmed cell death.

The "Autophagy" is a self-degradative process that is important for balancing sources of energy at critical times in development and in response to nutrient stress. Autophagy also plays a housekeeping role in removing misfolded or aggregated proteins, clearing damaged organelles, such as mitochondria, endoplasmic reticulum and peroxisomes, as well as eliminating intracellular pathogens.

The "explants" is living tissue transferred from an organism to an artificial medium for culture. "Photo-morphogenesis" is light-mediated development of plants.

The present invention relates to the development of a regulated expression module where tapetum-specific post-meiotic expression of a candidate gene can be achieved and their expression can abolished completely in the $F_1$ when crossed with transgenic containing second module. The invention provides a method which facilitates the use of male sterility related gene expression to achieve male-sterile plants and also restoration of fertility of $F_1$ hybrid which is pre-requisite for development of hybrid seed.

In one embodiment of the invention three expression vectors were constructed. The first vector construct is expression system (ES) consist of two transcription units (TUs); expression component and regulatory component (FIG. 1A). In first transcription unit (expression component) comprising a reporter gene which may be selected from gusA, GFP, YFP etc. under the transcriptional control of tapetum-specific promoter with mutated TATA-box to TGTA and suitable transcription termination signal including a polyadenylation signal.

The individual component of first transcriptional unit (TUs) are discussed: (a) $TA_{29(TGTA)}$; a tapetum-specific promoter from tobacco. TGTATATG mutation was introduced in the TATATATG box. This site directed mutagenesis makes it specific to TBPm3. It do not recognize native TATA-binding protein (TBP) but when tree amino acid replacement was made to form TBPm3, mutated TATA-box will recognize and higher expression will be achieved due to increased pool of TBPm3 dedicated to expression of $TA_{29(TGTA)}$ tagged transcript. ($TA_{29}$ promoter used from *Nicotiana tabacum*, TBPm3 gene from *Arabidopsis thaliana*. *Nicotiana tabacum* cv Petite Havana SR1, of LEHLE Seeds, United State. *Arabidopsis* genotype of *Arabidopsis* Biological Resource Centre (ABRC). (b) gusA; reporter gene encode β-glucuronidase which can be measured in terms of quantity as well as qualitative (tissue specificity). (Of pBI101 vector). (c) nosT; transcriptional terminator sequence including polyadenylation signal (of pBI101 vector).

The second transcriptional unit (TU) of ES (regulatory component) which regulates first TUs comprises of fusion polypeptide of the HFR1''-51$^{31}$-TBPm3 under the control of constitutive promoter and fused to a suitable transcription termination signal including a polyadenylation signal. The individual component of second transcriptional unit (TUs) are discussed: (a) Pcec; an artificial constitutive promoter (designed in our laboratory at CSIR-NBRI, Lucknow). (b) HFR1$^{n}$-1$^{31}$; Long hypocotyls in far red, a transcription factor of light regulated promoter which plays role in photo-morphogenesis. Only N-terminus fragment of 131 amino acids was taken which do not have any functional domain. It contain only interacting domain with repressor of light signaling i.e. COP1 (Constitutive photomorphogenic1). Therefore, expressions of HFR1$^{n-131}$ do not have any effect on the normal development on the plant (Yang J, Lin R, Sullivan J, Hoecker U, Liu B, Xu L, Deng X W, Wang H. (2005) Light regulates COP1-mediated degradation of HFR1, a transcription factor essential for light signaling in *Arabidopsis* Plant Cell, 17(3):804-21.). (HFR1$^{n-131}$ gene used from *Arabidopsis thaliana*. (c) TBPm3; TATA binding protein (TBP) with three amino acid substitutions: Ile$_{152}$ to Phe$_{152}$, Val$_{161}$ to Thr$_{161}$, and Leu$_{163}$ to Val$_{63}$. The three amino acid substitutions resulted in the change in protein conformation that makes it specific to mutated TATA box recognition. (of *Arabidopsis thaliana*). (d) nosT; transcriptional terminator sequence including a polyadenylation signal.

The sequence of ES construct is tapetum-specific promoter: reporter gene:transcriptional terminator:constitutive promoter: transcription factor fragment with ability to bind to restorer protein-TATA binding protein:transcriptional terminator, More specifically (TA29$_{(TGTA)}$:gusA:Tnos::Pcec:HFR1$^{n-131}$-TBPm3:Tnos) (FIG. 1A).

The second vector construct is male sterility (MS) module (FIG. 1B). The expression system similar to the first module except the reporter gene (gusA) is replaced by one of the several gene that impairs the tapetal degeneration and cause male sterility (described in prior art). In present invention *Arabidopsis* BECLIN1 gene (BECLIN1 gene from *Arabidopsis thaliana*) which is an autophagy related gene, when expressed in tapetum resulted male sterility. (Sudhir Pratap Singh, Tripti Pandey, Rakesh Srivastav, Praveen C. Verma, Praduman K. Singh, Rakesh Tuli and Samir V. Sawant (2010) BECLIN 1 from *Arabidopsis thaliana* under the generic control of regulated expression systems, a strategy for developing male sterile plants. Plant Biotech. J. 8, 1005-1022).

The third vector construct is restoration (RS) module (Figure. IC) consist of the single transcription unit where a protein that regulates the expression of first/second vector is expressed under the control of another tapetum-specific promoter with a suitable transcription termination signal including a polyadenylation signal. The RS module comprises: (a) A9; tapetum-specific promoter isolated from *Arabidopsis*. It express gene in the tapetum in postmeiotic anther stage of development. (A9 promoter from *Arabidopsis thaliana*). (b) COP1$^{L105A}$; Constitutive photomorphogenic1 (COP1) is a repressor of photo-morphogenesis. It functions as an essential negative regulator of light mediated plant development. It targets photo-morphogenesis promoting transcription factors like HYH, HY5, and HFR1 etc. for ubiquitylation and degradation in the dark and promote skoto-morphogenesis. The mutation in L105A in the nuclear exclusion sequence resulted increased nuclear localization while retaining functionality (Subramanian, C, Kim, D H, Lyssenko, N N, Xu, X, Johnson, C H and Arnim, AGV (2004) The *Arabidopsis* repressor of light signaling, COP1, is regulated by nuclear exclusion; mutational analysis by bioluminescence resonance energy transfer. PNAS, 101, 6798-6802). (COP1$^{L105A}$ gene from *Arabidopsis thaliana*). (c) nosT; transcriptional terminator sequence including a polyadenylation signal.

Figure 2A:
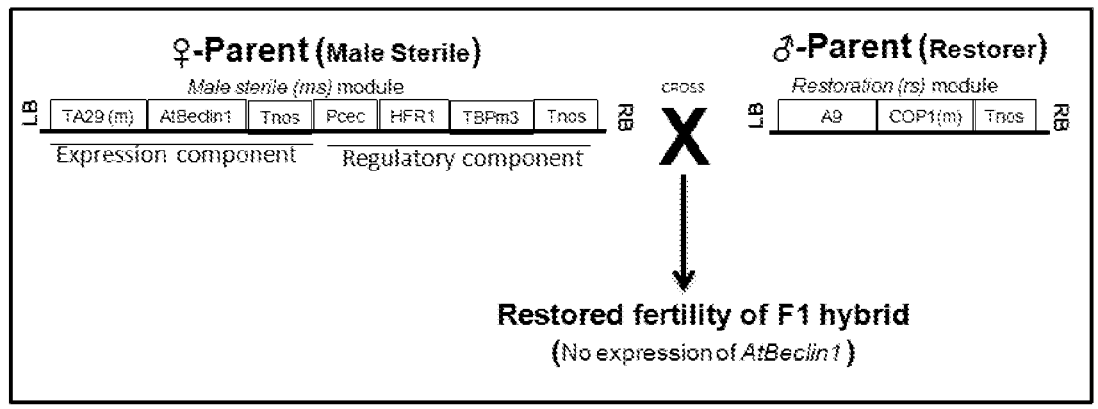

Another embodiment is to develop method where reversible expression of said gene can be achieved. The strategy underlying to achieve male sterile plant and restoring the fertility of F1 hybrid through transcription regulation and light signaling mechanism (FIG. 2A) is, MS construct will be transformed in parent which will be taken as female parent (male sterile) in hybrid breeding while RS construct will be transformed in the parent which will be taken as male parent (male fertile).The cross is made MS (female)xRS (male) to raise the F$_1$.

The ms module (FIG. 2B) is based on TGTA-TBPm3 complementation principle based two component system (Chaturvedi, C P, Lodhi, N, Ansari S A, Tiwari S, Srivastav R, Sawant S V, Tuli, R (2007) Mutated TATA-box/TATA binding protein complementation system for regulated transgene expression in tobacco. The Plant Journal 50, 917-925); it contains two transcriptional units (TUs), expression component and regulatory component. In first TU (expression component), AtBECLIN1 gene expressed using tobacco tapetum-specific promoter TA$_{29}$ with mutated TATA-box to TGTA. The TA$_{29(TGTA)}$ express AtBECLIN1 which is regulated by second TU (regulatory system). The regulatory system express fusion protein; only 311 amino acid N-terminus fragment of Long hypocotyls in Far-red (HFR1) SEQ ID-5, (a b-HLH transcription factor of light regulated promoters of *Arabidopsis*) and mutated version of TATA-binding protein TBPm3. HFR1$^{n-131aa}$-TBPm3 fusion protein express which recognize the TGTA of TA29 promoter and form pre-initiation complex (PIC). TBPm3 pool is available only to TGTA, therefore, high-level of AtBECLIN1 expression occurs in anther tapetum. Their expression will confer the complete male sterility.

Restoration (rs) module developed by expressing the *Arabidopsis* COP1 (constitutive photomorphogenic 1) in the anther tapetum using *Arabidopsis* tapetum-specific promoter A9. COP1 is repressor of Photomorphogenic development; it possesses E3 ligase activity toward a group of photo-morphogenesis promoting factors, including HFR1 and is responsible for their targeted degradation. Mutation in COP1$^{L105A}$ (SEQ ID-7) resulted in increased nuclear localization. A9 promoter confers the COP1$^{L105A}$ expression in the anther tapetum. Their expression do not alter the natural tapetal degeneration mechanism, hence, transgenic expressing COP1$^{L105A}$ are male fertile and are used as male-parent in hybrid development.

Figure 2D:
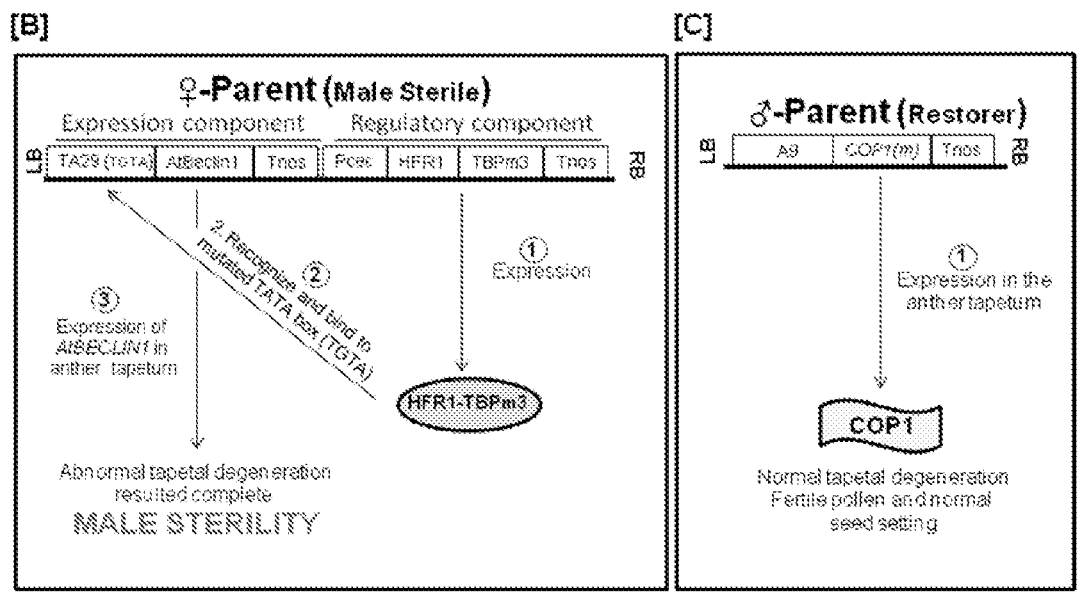
Figure 2D:
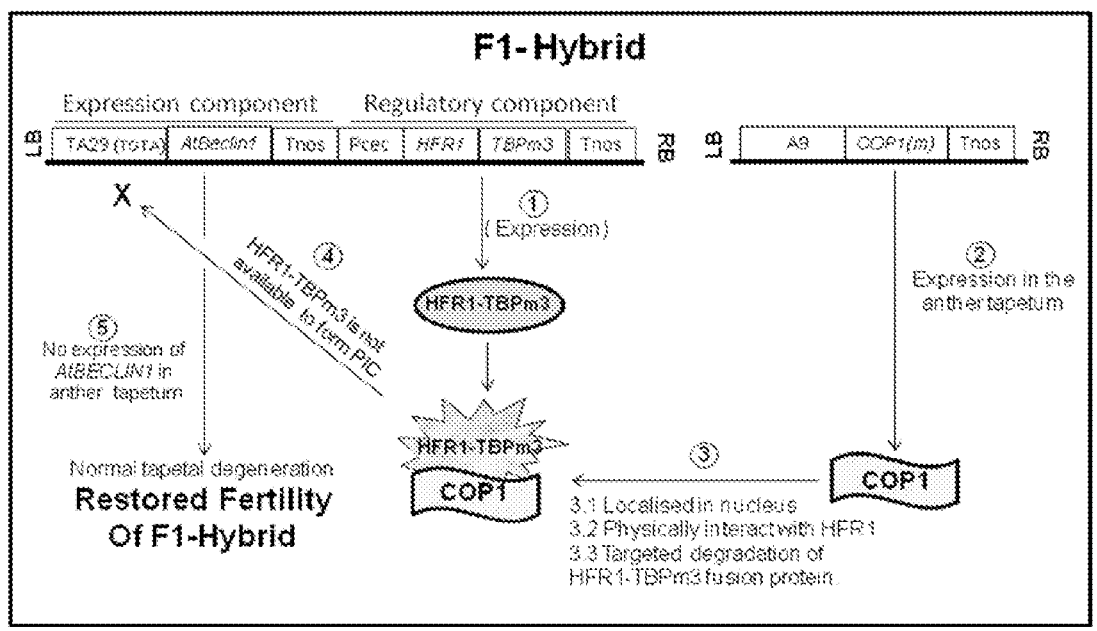

F1-hybrids were developed by crossing ms module expressing transgenic (female-parent) and restorer module expressing transgenic (male-parent) (Figure. 2D). In them, both module express in same tapetal cell. COP1$^{L105A}$ protein form which localized in the nucleus where it physically interact with HFR1$^{n-131aa}$ fragment of fusion protein HFR1$^{n-131aa}$-TBPm3 and resulted in the degradation of complete protein. TBPm3 will not available to form PIC, this results no expression of AtBECLIN1, normal tapetal degeneration and hence fertility of F1 hybrid will be restored.

Another embodiment *Agrobacterium* (of DNA cloning service (DCS), Germany) mediated transformation method comprises: (a) Constructing a recombinant construct; ES and MS expression systems were cloned in a binary vector pBI101 pBI101, and pBI121 (of Clontech, USA) separately in which nptII gene is used to express by constitutive promoter (CamV35S) which give resistance to kanamycine. The RS expression system cloned in binary vector where hptII gene expressed by weak constitutive promoter (pNOS) to avoid bidirectional expression, it gives resistance to hygromycine; (b) mobilizing the recombinant constructs of step (a) into *Agrobacterium* strain to produce recombinant *Agrobacterium* strains; (c) obtaining a suitable explant from the plant; (d) cultivating the explant with the recombinant *Agrobacterium* strain of step (b) to produce transformed plant cells; (e) culturing the transformed plant cells to produce transformed plants; (f) obtaining transformed plants.

The present invention relates to monocotyledonous or a dicotyledonous plant transformation, wherein the plant is selected from a group consisting of tobacco, cotton, rice, wheat, corn, potato, tomato, oilseed rape, alfalfa, sunflower, onion, clover, soyabean, pea.

One embodiment provides *Agrobacterium* strain selected from a group consisting of LBA4404, EHA 101 and EHA 105.

Another embodiment provides explant selected from a group consisting of leaf, stem, root, hypocotyl and embryo.

Yet another embodiment provides a transformed plant cell comprising the recombinant construct.

Still another embodiment provides a transgenic plant transformed with the recombinant constructs.

Another embodiment provides the transgenic plant selected from a group consisting of tobacco, cotton, rice, brassica, potato, tomato, oilseed rape, alfalfa, sunflower, onion, clover, soyabean, pea.

Yet another embodiment provides a plant, a plant part, a seed, a plant cell and a progeny thereof, wherein the plant, plant part, seed, plant cell, or progeny thereof comprises the recombinant construct.

Figure 3:
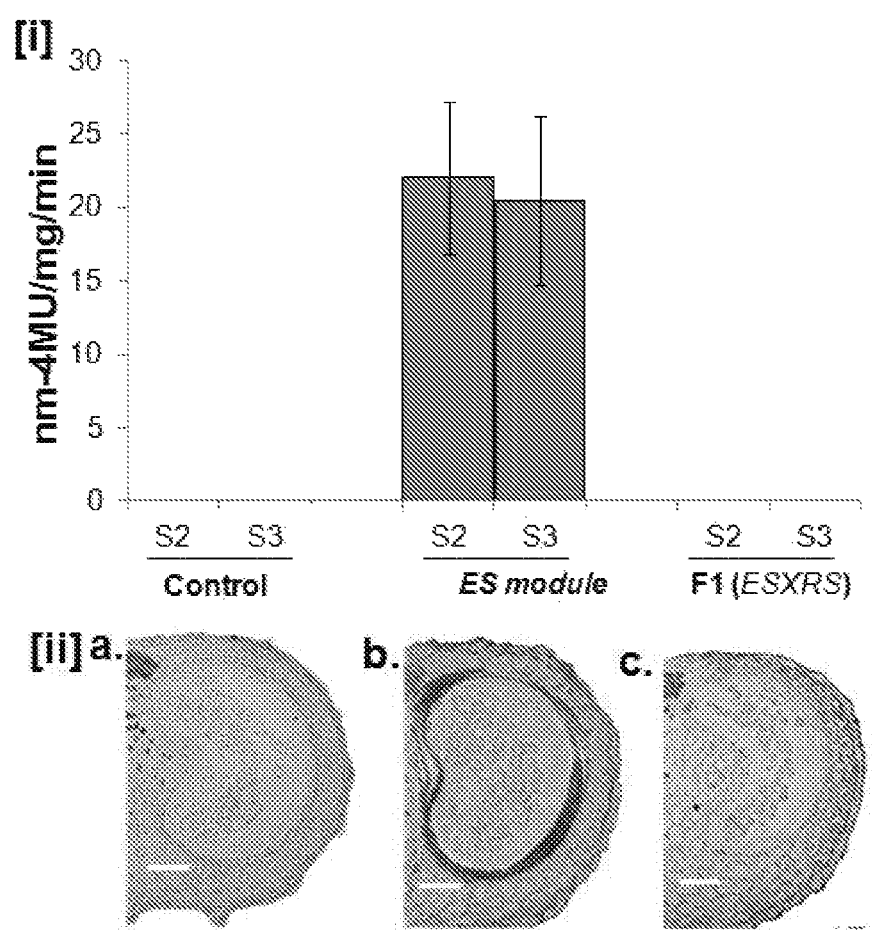

The present invention relates to a recombinant construct (FIG. 1A) for transforming plants to achieve tapetum-specific expression. Further, when another plant transformed with other recombinant construct (FIG. 1C) pollens used to cross the first one to raise $F_1$, the expression of said gene will be completely abolished. The said hypothesis was tested in tobacco by expressing gusA gene. Fluorometric GUS assay of post-meiotic anther of transgenic showing elevated expression of reporter gene, while F1 showing abolished expression (FIG. 3-*i*). When histochemical GUS staining was performed to localize the expressed gene, GUS staining localized in tapetum tissue of post-meiotic anther and no staining was appear in other plant tissue also no staining was appear in the $F_1$ tapetum of the same anther stage (FIG. 3-*ii*).

Tapetum is the innermost wall layer of the male reproductive organ anther in flowering plants. Post meiotic PCD like degeneration of tapetum is crucial for pollen fertility. Tapetum degeneration at post-meiotic stage of pollen development is requires as it releases nutrients to developing microspores, pollen wall materials, callase to separate the tetrad and other enzymes, flavenoids, alkenes, proteins etc. Alteration in the tapetal PCD (early/delayed) resulted in abortive pollen formation. Various genes were expressed to disrupt normal tapetal degeneration and male sterility was achieves; Barnase, RNase T-I, Mammalian uncoupling protein, Diphtheria toxin A-chain, Ribosome Inactivating Protein, BAX, *Arabidopsis* Bax inhibitor-1, AtBECLIN1 (discussed in prior art). The said method of the tapetum-specific expression of any gene that interferes in the normal tapetal degeneration mechanism will resulted in the male sterility. The above said vector construct are designed for tapetum-specific expression using tapetum-specific promoter but two level of stringency and higher level of expression make it better as it will be helpful in generating complete male sterile plants. Here we use AtBECLIN1 gene which is a plant autophagy related gene without cytotoxic role.

Figure 4:
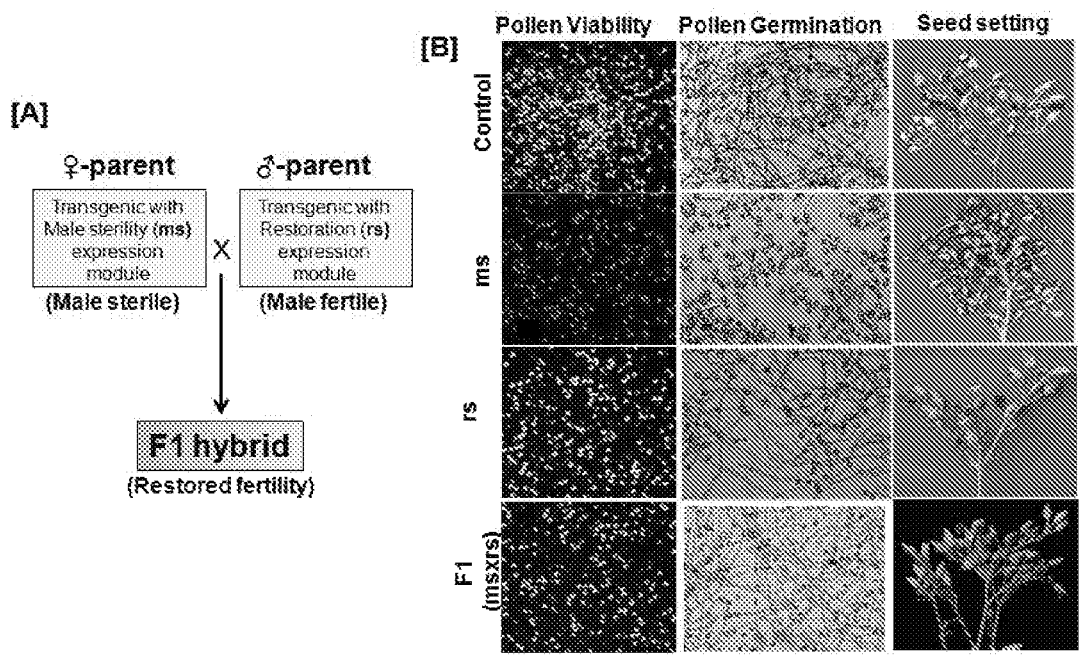

An embodiment of the present invention relates to a recombinant construct (FIG. 1B) expressing plant gene BECLIN1 in tapetum of post-meiotic anther (FIG. 6A). The expression vector includes restoration factor HFR1 which inclusion do not affect their expression. Their expression interfere normal tapetal degeneration causes pollen abortion and generates male sterile plant as was reported previously (FIG. 4B). These plants fail to produce viable pollen (FIG. 5A) and are not able to facilitate normal seed setting (FIG. 6B).

For the production of hybrid seeds which is aim of hybrid breeding, male sterility based hybrids have several advantages and are cheaper as it replace the manual emasculation process. When the commercial product is hybrid seed, there is need to restore the fertility of F1 hybrid. In present condition effective restoration of F1 fertility is limitation. Here our said method provides effective restoration of F1 hybrid with broad applicability. The method is advanced as the control of the male sterility gene is at transcription level.

Figure 5:
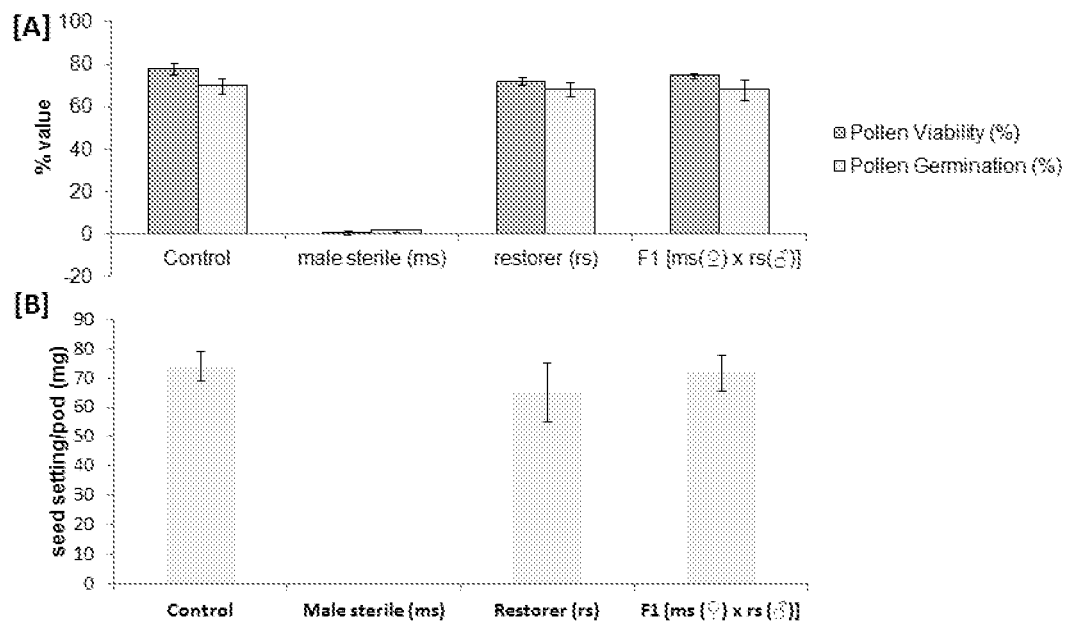
FIG. 5A depicts in-vitro pollen viability (pv) and pollen germination (pg) assay; Transgenic with male sterile (ms) module shows complete abortion of pollen while in restorer plant shows normal fertility, in F1-hybrid the pollen fertility restored similar to the control plant (n=10).
FIG. 5B depicts seed setting per pod (in mg); in ms transgenic no seed setting was observed while in rs transgenic normal seed setting, when F1 raise the normal seed setting restored (n=10).
Figure 6:
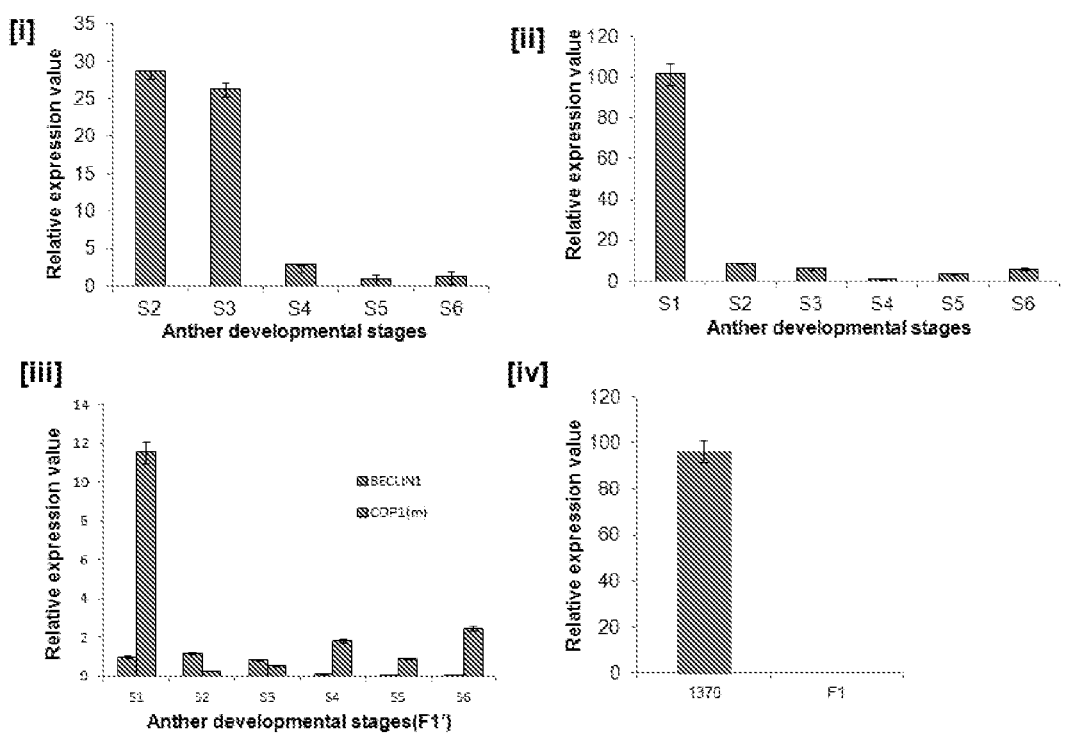
FIG. 6i depicts the relative expression of BECLIN1 in different anther development stages (S2-S6) of MS transgenic, it's predominantly express in S2 and S3 stage of the anther development. UBIQ was used for normalization, and the error bars indicate the SD of three independent experiments.

Another embodiment of the present invention relates to a recombinant construct (FIG. 1C) wherein said regulatory sequence (COP1$^{L105A}$) is expressed using suitable promoter i.e. tapetum specific promoter (A9) having polynucleotide sequence as shown in SEQ ID NO: 7. it express COP1$^{L105A}$) post-meiotic but prior to the BECLIN1 (FIG. 6-*ii*). The transgenic of the said are fertile (FIG. 4B, 5A) and showing normal seed settings (FIG. 4B, 5B) . . . .

Yet another embodiment of the present invention relates to the crossing of the ms transgenic (♀) and rs transgenic (♂) to raise the $F_1$ plants.

Still another embodiment is to analyses $F_1$ plants, they are showing restored fertility as pollen viability and pollen germination is similar to control plant (FIG. 4B, 5A) and normal seed setting (FIG. 4B, 5B). When expression of BECLIN1 was checked in different anther developmental stages, it was found that their expression was abolished (FIGS. 6-*iii* and 6-*iv*).

Hybrid crops are made to exploit heterosis or hybrid vigor. Heterosis is exhibited when two heterotic parents P1 (♀) and P2 (♂) will cross to make $F_1$. The ♀ above said method can be established in such that P1 parents will be transformed with MS vector and P2 with RS vector. P1 will be complete male sterile while P2 will show normal fertility. When both crossed [P1 (♀)xP2 (♂)], II rose with restored fertility. The method can be established in previously defined heterotic parents.

In an embodiment of the present disclosure, there is provided a MS DNA construct comprising: (a) a first expression cassette comprising a first tissue specific promoter operably linked to a desired gene of interest, expression of which leads to male sterility in plants, and a terminator; and (b) a second regulatory cassette comprising a second promoter operably linked to a fragment encoding a fusion peptide of N-terminal fragment of a transcription factor and TBPm3 having SEQ ID NO: 6, and a terminator.

In an embodiment of the present disclosure, there is provided a MS DNA construct as described herein, wherein said first tissue specific promoter is tapetum specific promoter TA29 having SEQ ID NO: 1.

In an embodiment of the present disclosure, there is provided a MS DNA construct as described herein, wherein said desired gene of interest is selected from the group consisting of BARNASE, RNase, T-I, Mammalian uncoupling protein, *Diptheria toxin* A-chain, BAX, and AtBECLIN1.

In an embodiment of the present disclosure, there is provided a MS DNA construct as described herein, wherein said desired gene of interest is AtBECLIN1 having SEQ ID NO: 2.

In an embodiment of the present disclosure, there is provided a MS DNA construct as described herein, wherein said second promoter is constitutive or tissue specific.

In an embodiment of the present disclosure, there is provided a MS DNA construct as described herein, wherein said second promoter is a constitutive promoter having SEQ ID NO: 4.

In an embodiment of the present disclosure, there is provided a MS DNA construct as described herein, wherein said terminator is Nos terminator having SEQ ID NO: 3.

In an embodiment of the present disclosure, there is provided a MS DNA construct as described herein, wherein said N-terminal fragment of a transcription factor is a 131 amino acid long fragment selected from the group consisting of HY5, HYH, and HFR1.

In an embodiment of the present disclosure, there is provided a MS DNA construct as described herein, wherein said N-terminal fragment of a transcription factor is a 131 amino acid long fragment from HFR1.

In an embodiment of the present disclosure, there is provided a MS DNA construct comprising: (a) a first expression cassette comprising a first tapetum specific promoter TA29 having SEQ ID NO: 1 operably linked to AtBECLIN1 having SEQ ID NO: 2, expression of which leads to male sterility in plants, and a Nos terminator having SEQ ID NO: 3; and (b) a second regulatory cassette comprising a second constitutive promoter having SEQ ID NO: 4 operably linked to a fragment encoding a fusion peptide of 131 amino acid long fragment from HFR1 and TBPm3 having SEQ ID NO: 6, and a Nos terminator having SEQ ID NO: 3.

In an embodiment of the present disclosure, there is provided a ES DNA construct comprising: (a) a first expression cassette comprising a first tissue specific promoter operably linked to a gene of interest, and a terminator; and (b) a second regulatory cassette comprising a second promoter operably linked to a fragment encoding a fusion peptide of N-terminal fragment of a transcription factor and TBPm3 having SEQ ID NO: 6, and a terminator.

In an embodiment of the present disclosure, there is provided a ES DNA construct as described herein, wherein said first tissue specific promoter is tapetum specific promoter TA29 having SEQ ID NO: 1.

In an embodiment of the present disclosure, there is provided a ES DNA construct as described herein, wherein said gene of interest is selected from the group consisting of gusA, GFP, YFP, LUX, nptI, nptII genes.

In an embodiment of the present disclosure, there is provided a ES DNA construct as described herein, wherein said terminator is Nos terminator having SEQ ID NO: 3.

In an embodiment of the present disclosure, there is provided a ES DNA construct as described herein, wherein said second promoter is constitutive or tissue specific.

In an embodiment of the present disclosure, there is provided a ES DNA construct as described herein, wherein said second promoter is a constitutive promoter having SEQ ID NO: 4.

In an embodiment of the present disclosure, there is provided a ES DNA construct as described herein, wherein said N-terminal fragment of a transcription factor is a 131 amino acid long fragment selected from the group consisting of HY5, HYH, and HFR1.

In an embodiment of the present disclosure, there is provided a ES DNA construct as described herein, wherein said N-terminal fragment of a transcription factor is a 131 amino acid long fragment from HFR1.

In an embodiment of the present disclosure, there is provided a ES DNA construct comprising: (a) a first expression cassette comprising a first tapetum specific promoter TA29 having SEQ ID NO: 1 operably linked to a gene of interest, and a Nos terminator having SEQ ID NO: 3; and (b) a second regulatory cassette comprising a second constitutive promoter having SEQ ID NO: 4 operably linked to a fragment encoding a fusion peptide of 131 amino acid long fragment from HFR1 and TBPm3 having SEQ ID NO: 6, and a terminator.

In an embodiment of the present disclosure, there is provided a RS DNA construct comprising an expression cassette comprising a third issue specific promoter operably linked to a restorer gene, and a terminator.

In an embodiment of the present disclosure, there is provided a RS DNA construct as described herein, wherein said third tissue specific promoter is tapetum specific promoter having SEQ ID NO: 7.

In an embodiment of the present disclosure, there is provided a RS DNA construct as described herein, wherein said restorer gene is a mutant COP1 having SEQ ID NO: 8.

In an embodiment of the present disclosure, there is provided a RS DNA construct as described herein, wherein said terminator is Nos terminator having SEQ ID NO: 3.

In an embodiment of the present disclosure, there is provided a RS DNA construct comprising an expression cassette comprising a third tapetum specific promoter having SEQ ID NO: 7 operably linked to a mutant COP1 having SEQ ID NO: 8, and a Nos terminator having SEQ ID NO: 3.

In an embodiment of the present disclosure, there is provided a reversible expression system for modulating male sterility in plants, said system comprising: (a) a first component consisting of: (i) a first expression cassette comprising: a first tissue specific promoter operably linked to a desired gene of interest, expression of which causes male sterility in plants, and a terminator; and (ii) a second regulatory cassette comprising: a second promoter operably linked to a fragment encoding a fusion peptide of N-terminal fragment of a transcription factor and TBPm3 having SEQ ID NO: 6, and a terminator; (b) a second component consisting of an expression cassette comprising: a third tissue specific promoter operably linked to a restorer gene, and a terminator.

In an embodiment of the present disclosure, there is provided a reversible expression system for modulating male sterility in plants as described herein, wherein said first tissue specific promoter is tapetum specific promoter TA29 having SEQ ID NO: 1.

In an embodiment of the present disclosure, there is provided a reversible expression system for modulating male sterility in plants as described herein, wherein said desired gene of interest is selected from the group consisting of BARNASE, RNase, T-I, Mammalian uncoupling protein, Diptheria toxin A-chain, BAX, and AtBECLIN1.

In an embodiment of the present disclosure, there is provided a reversible expression system for modulating male sterility in plants as described herein, wherein said desired gene of interest is AtBECLIN1 having SEQ ID NO: 2.

In an embodiment of the present disclosure, there is provided a reversible expression system for modulating male sterility in plants as described herein, wherein said terminator is Nos terminator having SEQ ID NO: 3.

In an embodiment of the present disclosure, there is provided a reversible expression system for modulating male sterility in plants as described herein, wherein said second promoter is constitutive or tissue specific.

In an embodiment of the present disclosure, there is provided a reversible expression system for modulating male sterility in plants as described herein, wherein said second promoter is a constitutive promoter having SEQ ID NO: 4.

In an embodiment of the present disclosure, there is provided a reversible expression system for modulating male sterility in plants as described herein, wherein said N-terminal fragment of a transcription factor is a 131 amino acid long fragment selected from the group consisting of HY5, HYH, and HFR1.

In an embodiment of the present disclosure, there is provided a reversible expression system for modulating male sterility in plants as described herein, wherein said N-terminal fragment of a transcription factor is a 131 amino acid long fragment from HFR1.

In an embodiment of the present disclosure, there is provided a reversible expression system for modulating male sterility in plants as described herein, wherein said third tissue specific promoter is tapetum specific promoter having SEQ ID NO: 7.

In an embodiment of the present disclosure, there is provided a reversible expression system for modulating male sterility in plants as described herein, wherein said restorer gene is a mutant COP1 having SEQ ID NO: 8.

In an embodiment of the present disclosure, there is provided a reversible expression system for modulating male sterility in plants, said system comprising: (a) a first component consisting of: (i) a first expression cassette comprising: a first tapetum specific promoter TA29 having SEQ ID NO: 1 operably linked to AtBECLIN1 having SEQ ID NO: 2, expression of which causes male sterility in plants, and a Nos terminator having SEQ ID NO: 3; and (ii) a second regulatory cassette comprising: a second constitutive promoter having SEQ ID NO: 4 operably linked to a fragment encoding a fusion peptide of N-terminal fragment of a 131 amino acid long fragment from HFR1 and TBPm3 having SEQ ID NO: 6, and a Nos terminator having SEQ ID NO: 3; (b) a second component consisting of an expression cassette comprising: a third tapetum specific promoter having SEQ ID NO: 7 operably linked to a mutant COP1 having SEQ ID NO: 8, and a Nos terminator having SEQ ID NO: 3.

In an embodiment of the present disclosure, there is provided a reversible expression system for modulating transgene expression in plants, said system comprising: (a) a first component consisting of: (i) a first expression cassette comprising: a first tissue specific promoter operably linked to a gene of interest, and a terminator; and (ii) a second regulatory cassette comprising: a second promoter operably linked to a fragment encoding a fusion peptide of N-terminal fragment of a transcription factor and TBPm3 having SEQ ID NO: 6, and a terminator; (b) a second component consisting of an expression cassette comprising: a third tissue specific promoter operably linked to a restorer gene, and a terminator.

In an embodiment of the present disclosure, there is provided a reversible expression system for modulating transgene expression in plants as described herein, wherein said first tissue specific promoter is tapetum specific promoter TA29 having SEQ ID NO: 1.

In an embodiment of the present disclosure, there is provided a reversible expression system for modulating transgene expression in plants as described herein, wherein said gene of interest is selected from the group consisting of gusA, GFP, YFP, LUX, nptI, nptII genes.

In an embodiment of the present disclosure, there is provided a reversible expression system for modulating transgene expression in plants as described herein, wherein said terminator is Nos terminator having SEQ ID NO: 3.

In an embodiment of the present disclosure, there is provided a reversible expression system for modulating transgene expression in plants as described herein, wherein said second promoter is constitutive or tissue specific.

In an embodiment of the present disclosure, there is provided a reversible expression system for modulating transgene expression in plants as described herein, wherein said second promoter is a constitutive promoter having SEQ ID NO: 4.

In an embodiment of the present disclosure, there is provided a reversible expression system for modulating transgene expression in plants as described herein, wherein said N-terminal fragment of a transcription factor is a 131 amino acid long fragment selected from the group consisting of HY5, HYH, and HFR1.

In an embodiment of the present disclosure, there is provided a reversible expression system for modulating transgene expression in plants as described herein, wherein said N-terminal fragment of a transcription factor is a 131 amino acid long fragment from HFR1.

In an embodiment of the present disclosure, there is provided a reversible expression system for modulating transgene expression in plants as described herein, wherein said third tissue specific promoter is tapetum specific promoter having SEQ ID NO: 7.

In an embodiment of the present disclosure, there is provided a reversible expression system for modulating transgene expression in plants as described herein, wherein said restorer gene is a mutant COP1 having SEQ ID NO: 8.

In an embodiment of the present disclosure, there is provided a reversible expression system for modulating transgene expression in plants, said system comprising: (a) a first expression cassette comprising: (i) a first tapetum specific promoter TA29 having SEQ ID NO: 1 operably linked to a gene of interest, and a Nos terminator having SEQ ID NO: 3; and (ii) a second regulatory cassette comprising: a second constitutive promoter having SEQ ID NO: 4 operably linked to a fragment encoding a fusion peptide of N-terminal fragment of a 131 amino acid long fragment from HFR1 and TBPm3 having SEQ ID NO: 6, and a Nos terminator having SEQ ID NO: 3; (b) a second component consisting of an expression cassette comprising: a third tapetum specific promoter having SEQ ID NO: 7 operably linked to a mutant COP1 having SEQ ID NO: 8, and a Nos terminator having SEQ ID NO: 3.

In an embodiment of the present disclosure, there is provided a DNA vector comprising a MS DNA construct, said MS DNA construct comprising: (a) a first expression cassette comprising a first tissue specific promoter operably linked to a desired gene of interest, expression of which leads to male sterility in plants, and a terminator; and (b) a second regulatory cassette comprising a second promoter operably linked to a fragment encoding a fusion peptide of N-terminal fragment of a transcription factor and TBPm3 having SEQ ID NO: 6, and a terminator.

In an embodiment of the present disclosure, there is provided a DNA vector comprising a ES DNA construct, said ES DNA construct comprising: (a) first expression cassette comprising a first tissue specific promoter operably linked to a gene of interest, and a terminator; and (b) a second regulatory cassette comprising a second promoter operably linked to a fragment encoding a fusion peptide of N-terminal fragment of a transcription factor and TBPm3 having SEQ ID NO: 6, and a terminator.

In an embodiment of the present disclosure, there is provided a DNA vector comprising a RS DNA construct, said RS DNA construct comprising an expression cassette comprising a third issue specific promoter operably linked to a restorer gene, and a terminator.

In an embodiment of the present disclosure, there is provided a DNA vector as described herein, wherein said first tissue specific promoter is tapetum specific promoter TA29 having SEQ ID NO: 1.

In an embodiment of the present disclosure, there is provided a DNA vector as described herein, wherein said desired gene of interest is selected from the group consisting of BARNASE, RNase, T-I, Mammalian uncoupling protein, Diptheria toxin A-chain, BAX, and AtBECLIN1.

In an embodiment of the present disclosure, there is provided a DNA vector as described herein, wherein said desired gene of interest is AtBECLIN1 having SEQ ID NO: 2.

In an embodiment of the present disclosure, there is provided a DNA vector as described herein, wherein said second promoter is constitutive or tissue specific.

In an embodiment of the present disclosure, there is provided a DNA vector as described herein, wherein said second promoter is a constitutive promoter having SEQ ID NO: 4.

In an embodiment of the present disclosure, there is provided a DNA vector as described herein, wherein said terminator is Nos terminator having SEQ ID NO: 3.

In an embodiment of the present disclosure, there is provided a DNA vector as described herein, wherein said N-terminal fragment of a transcription factor is a 131 amino acid long fragment selected from the group consisting of HY5, HYH, and HFR1.

In an embodiment of the present disclosure, there is provided a DNA vector as described herein, wherein said N-terminal fragment of a transcription factor is a 131 amino acid long fragment from HFR1.

In an embodiment of the present disclosure, there is provided a DNA vector as described herein, wherein said gene of interest is selected from the group consisting of gusA, GFP, YFP, LUX, nptI, nptII genes.

In an embodiment of the present disclosure, there is provided a DNA vector as described herein, wherein said third tissue specific promoter is tapetum specific promoter having SEQ ID NO: 7.

In an embodiment of the present disclosure, there is provided a DNA vector as described herein, wherein said restorer gene is a mutant COP1 having SEQ ID NO: 8.

In an embodiment of the present disclosure, there is provided a DNA vector comprising a MS DNA construct, said MS DNA construct comprising: (a) a first expression cassette comprising a first tapetum specific promoter TA29 having SEQ ID NO: 1 operably linked to AtBECLIN1 having SEQ ID NO: 2, expression of which leads to male sterility in plants, and a Nos terminator having SEQ ID NO: 3; and (b) a second regulatory cassette comprising a second constitutive promoter having SEQ ID NO: 4 operably linked to a fragment encoding a fusion peptide of 131 amino acid long fragment from HFR1 and TBPm3 having SEQ ID NO: 6, and a Nos terminator having SEQ ID NO: 3.

In an embodiment of the present disclosure, there is provided a DNA vector comprising a ES DNA construct, said ES DNA construct comprising: (a) a first expression cassette comprising a first tapetum specific promoter TA29 having SEQ ID NO: 1 operably linked to a gene of interest, and a Nos terminator having SEQ ID NO: 3; and (b) a second regulatory cassette comprising a second constitutive promoter having SEQ ID NO: 4 operably linked to a fragment encoding a fusion peptide of 131 amino acid long fragment from HFR1 and TBPm3 having SEQ ID NO: 6, and a Nos terminator having SEQ ID NO: 3.

In an embodiment of the present disclosure, there is provided a DNA vector comprising a RS DNA construct, said RS DNA construct comprising an expression cassette comprising a third tapetum specific promoter having SEQ ID NO: 7 operably linked to a mutant COP1 having SEQ ID NO: 8, and a Nos terminator having SEQ ID NO: 3.

In an embodiment of the present disclosure, there is provided a recombinant host cell comprising a MS DNA construct, said MS DNA construct comprising: (a) a first expression cassette comprising a first tissue specific promoter operably linked to a desired gene of interest, expression of which leads to male sterility in plants, and a terminator; and (b) a second regulatory cassette comprising a second promoter operably linked to a fragment encoding a fusion peptide of N-terminal fragment of a transcription factor and TBPm3 having SEQ ID NO: 6, and a terminator.

In an embodiment of the present disclosure, there is provided a recombinant host cell comprising a ES DNA construct, said ES DNA construct comprising: (a) a first expression cassette comprising a first tissue specific promoter operably linked to a gene of interest, and a terminator; and (b) a second regulatory cassette comprising a second promoter operably linked to a fragment encoding a fusion peptide of N-terminal fragment of a transcription factor and TBPm3 having SEQ ID NO: 6, and a terminator.

In an embodiment of the present disclosure, there is provided a recombinant host cell comprising a RS DNA construct, said RS DNA construct comprising an expression cassette comprising a third issue specific promoter operably linked to a restorer gene, and a terminator.

In an embodiment of the present disclosure, there is provided a recombinant host cell comprising a DNA vector, said DNA vector comprising a MS DNA construct comprising: (a) a first expression cassette comprising a first tissue specific promoter operably linked to a desired gene of interest, expression of which leads to male sterility in plants, and a terminator; and (b) a second regulatory cassette comprising a second promoter operably linked to a fragment encoding a fusion peptide of N-terminal fragment of a transcription factor and TBPm3 having SEQ ID NO: 6, and a terminator.

In an embodiment of the present disclosure, there is provided a recombinant host cell comprising a DNA vector, said DNA vector comprising a ES DNA construct comprising: (a) a first expression cassette comprising a first tissue specific promoter operably linked to a gene of interest, and a terminator; and (b) a second regulatory cassette comprising a second promoter operably linked to a fragment encoding a fusion peptide of N-terminal fragment of a transcription factor and TBPm3 having SEQ ID NO: 6, and a terminator.

In an embodiment of the present disclosure, there is provided a recombinant host cell comprising a DNA vector, said DNA vector comprising a RS DNA construct comprising an expression cassette comprising a third issue specific promoter operably linked to a restorer gene, and a terminator.

In an embodiment of the present disclosure, there is provided a recombinant host cell as described herein, wherein said first tissue specific promoter is tapetum specific promoter TA29 having SEQ ID NO: 1.

In an embodiment of the present disclosure, there is provided a recombinant host cell as described herein, wherein said desired gene of interest is selected from the group consisting of BARNASE, RNase, T-I, Mammalian uncoupling protein, Diptheria toxin A-chain, BAX, and AtBECLIN1.

In an embodiment of the present disclosure, there is provided a recombinant host cell as described herein, wherein said desired gene of interest is AtBECLIN1 having SEQ ID NO: 2.

In an embodiment of the present disclosure, there is provided a recombinant host cell as described herein, wherein said second promoter is constitutive or tissue specific.

In an embodiment of the present disclosure, there is provided a recombinant host cell as described herein, wherein said second promoter is a constitutive promoter having SEQ ID NO: 4.

In an embodiment of the present disclosure, there is provided a recombinant host cell as described herein, wherein said terminator is Nos terminator having SEQ ID NO: 3.

In an embodiment of the present disclosure, there is provided a recombinant host cell as described herein, wherein said N-terminal fragment of a transcription factor is a 131 amino acid long fragment selected from the group consisting of HY5, HYH, and HFR1.

In an embodiment of the present disclosure, there is provided a recombinant host cell as described herein, wherein said N-terminal fragment of a transcription factor is a 131 amino acid long fragment from HFR1.

In an embodiment of the present disclosure, there is provided a recombinant host cell as described herein, wherein said gene of interest is selected from the group consisting of gusA, GFP, YFP, LUX, nptI, nptII genes.

In an embodiment of the present disclosure, there is provided a recombinant host cell as described herein, wherein said third tissue specific promoter is tapetum specific promoter having SEQ ID NO: 7.

In an embodiment of the present disclosure, there is provided a recombinant host cell as described herein, wherein said restorer gene is a mutant COP1 having SEQ ID NO: 8.

In an embodiment of the present disclosure, there is provided a recombinant host cell as described herein, wherein said recombinant host cell is a plant cell.

In an embodiment of the present disclosure, there is provided a recombinant host cell as described herein, wherein said recombinant host cell is *Agrobacterium tumefaciens*.

In an embodiment of the present disclosure, there is provided a recombinant host cell comprising a MS DNA construct comprising: (a) a first expression cassette comprising a first tapetum specific promoter TA29 having SEQ ID NO: 1 operably linked to AtBECLIN1 having SEQ ID NO: 2, expression of which leads to male sterility in plants, and a Nos terminator having SEQ ID NO: 3; and (b) a second regulatory cassette comprising a second constitutive promoter having SEQ ID NO: 4 operably linked to a fragment encoding a fusion peptide of 131 amino acid long fragment from HFR1 and TBPm3 having SEQ ID NO: 6, and a terminator.

In an embodiment of the present disclosure, there is provided a recombinant host cell comprising a DNA vector, said DNA vector comprising a MS DNA construct comprising: (a) a first expression cassette comprising a first tapetum specific promoter TA29 having SEQ ID NO: 1 operably linked to AtBECLIN1 having SEQ ID NO: 2, expression of which leads to male sterility in plants, and a Nos terminator having SEQ ID NO: 3; and (b) a second regulatory cassette comprising a second constitutive promoter having SEQ ID NO: 4 operably linked to a fragment encoding a fusion peptide of 131 amino acid long fragment from HFR1 and TBPm3 having SEQ ID NO: 6, and a terminator.

In an embodiment of the present disclosure, there is provide a recombinant host cell comprising a ES DNA construct comprising: (a) a first expression cassette comprising a first tapetum specific promoter TA29 having SEQ ID NO: 1 operably linked to a gene of interest, and a Nos terminator having SEQ ID NO: 3; and (b) a second regulatory cassette comprising a second constitutive promoter having SEQ ID NO: 4 operably linked to a fragment encoding a fusion peptide of 131 amino acid long fragment from HFR1 and TBPm3 having SEQ ID NO: 6, and a terminator.

In an embodiment of the present disclosure, there is provide a recombinant host cell comprising a DNA vector, said DNA vector comprising a ES DNA construct comprising: (a) a first expression cassette comprising a first tapetum specific promoter TA29 having SEQ ID NO: 1 operably linked to a gene of interest, and a Nos terminator having SEQ ID NO: 3; and (b) a second regulatory cassette comprising a second constitutive promoter having SEQ ID NO: 4 operably linked to a fragment encoding a fusion peptide of 131 amino acid long fragment from HFR1 and TBPm3 having SEQ ID NO: 6, and a terminator.

In an embodiment of the present disclosure, there is provided a recombinant host cell comprising a RS DNA construct comprising an expression cassette comprising a third tapetum specific promoter having SEQ ID NO: 7 operably linked to a mutant COP1 having SEQ ID NO: 8, and a Nos terminator having SEQ ID NO: 3.

In an embodiment of the present disclosure, there is provided a recombinant host cell comprising a DNA vector, said DNA vector comprising a RS DNA construct comprising an expression cassette comprising a third tapetum specific promoter having SEQ ID NO: 7 operably linked to a mutant COP1 having SEQ ID NO: 8, and a Nos terminator having SEQ ID NO: 3.

In an embodiment of the present disclosure, there is provided a transgenic plant or parts thereof, including seeds comprising a MS DNA construct comprising: (a) a first expression cassette comprising a first tissue specific promoter operably linked to a desired gene of interest, expression of which leads to male sterility in plants, and a terminator; and (b) a second regulatory cassette comprising a second promoter operably linked to a fragment encoding a fusion peptide of N-terminal fragment of a transcription factor and TBPm3 having SEQ ID NO: 6, and a terminator, wherein the transgenic plant is male sterile.

In an embodiment of the present disclosure, there is provided a transgenic plant or parts thereof, including seeds comprising a RS DNA construct comprising a third issue specific promoter operably linked to a restorer gene, and a terminator, wherein said transgenic plant is capable of restoring male sterility.

In an embodiment of the present disclosure, there is provided a transgenic plant or parts thereof, including seeds comprising a ES DNA construct comprising: (a) a first expression cassette comprising a first tissue specific promoter operably linked to a gene of interest, and a terminator; and (b) a second regulatory cassette comprising a second promoter operably linked to a fragment encoding a fusion peptide of N-terminal fragment of a transcription factor and TBPm3 having SEQ ID NO: 6, and a terminator, wherein said plant is capable of expression of a gene of interest.

In an embodiment of the present disclosure, there is provided a transgenic plant or parts thereof, including seeds comprising a RS DNA construct comprising a third issue specific promoter operably linked to a restorer gene, and a terminator, wherein said plant is capable of inhibiting expression of a gene of interest.

In an embodiment of the present disclosure, there is provided a transgenic plant as described herein, wherein said first tissue specific promoter is tapetum specific promoter TA29 having SEQ ID NO: 1.

In an embodiment of the present disclosure, there is provided a transgenic plant as described herein, wherein said desired gene of interest is selected from the group consisting of BARNASE, RNase, T-I, Mammalian uncoupling protein, Diptheria toxin A-chain, BAX, and AtBECLIN1.

In an embodiment of the present disclosure, there is provided a transgenic plant as described herein, wherein said desired gene of interest is AtBECLIN1 having SEQ ID NO: 2.

In an embodiment of the present disclosure, there is provided a transgenic plant as described herein, wherein said second promoter is constitutive or tissue specific.

In an embodiment of the present disclosure, there is provided a transgenic plant as described herein, wherein said second promoter is a constitutive promoter having SEQ ID NO: 4.

In an embodiment of the present disclosure, there is provided a transgenic plant as described herein, wherein said terminator is Nos terminator having SEQ ID NO: 3.

In an embodiment of the present disclosure, there is provided a transgenic plant as described herein, wherein said N-terminal fragment of a transcription factor is a 131 amino acid long fragment selected from the group consisting of HY5, HYH, and HFR1.

In an embodiment of the present disclosure, there is provided a transgenic plant as described herein, wherein said N-terminal fragment of a transcription factor is a 131 amino acid long fragment from HFR1.

In an embodiment of the present disclosure, there is provided a transgenic plant as described herein, wherein said gene of interest is selected from the group consisting of gusA, GFP, YFP, LUX, nptI, nptII genes.

In an embodiment of the present disclosure, there is provided a transgenic plant as described herein, wherein said third tissue specific promoter is tapetum specific promoter having SEQ ID NO: 7.

In an embodiment of the present disclosure, there is provided a transgenic plant as described herein, wherein restorer gene is a mutant COP1 having SEQ ID NO: 8.

In an embodiment of the present disclosure, there is provided a transgenic plant or parts thereof, including seeds comprising a MS DNA construct comprising: (a) a first expression cassette comprising a first tapetum specific promoter TA29 having SEQ ID NO: 1 operably linked to AtBECLIN1 having SEQ ID NO: 2, expression of which leads to male sterility in plants, and a Nos terminator having SEQ ID NO: 3; and (b) a second regulatory cassette comprising a second constitutive promoter having SEQ ID NO: 4 operably linked to a fragment encoding a fusion peptide of 131 amino acid long fragment from HFR1 and TBPm3 having SEQ ID NO: 6, and a Nos terminator having SEQ ID NO: 3, wherein said transgenic plant is male sterile.

In an embodiment of the present disclosure, there is provided a transgenic plant or parts thereof, including seeds comprising a RS DNA construct comprising an expression cassette comprising a third tapetum specific promoter having SEQ ID NO: 7 operably linked to a mutant COP1 having SEQ ID NO: 8, and a Nos terminator having SEQ ID NO: 3, wherein said plant is capable of restoring male sterility.

In an embodiment of the present disclosure, there is provided a transgenic plant or parts thereof, including seeds comprising a RS DNA construct comprising an expression cassette comprising a third tapetum specific promoter having SEQ ID NO: 7 operably linked to a mutant COP1 having SEQ ID NO: 8, and a Nos terminator having SEQ ID NO: 3, wherein said plant is capable of inhibiting expression of a gene of interest.

In an embodiment of the present disclosure, there is provided a transgenic plant or parts thereof, including seeds comprising a ES DNA construct comprising: (a) a first expression cassette comprising a first tapetum specific promoter TA29 having SEQ ID NO: 1 operably linked to a gene of interest, and a Nos terminator having SEQ ID NO: 3; and (b) a second regulatory cassette comprising a second constitutive promoter having SEQ ID NO: 4 operably linked to a fragment encoding a fusion peptide of 131 amino acid long fragment from HFR1 and TBPm3 having SEQ ID NO: 6, and a Nos terminator having SEQ ID NO: 3, wherein said plant is capable of expression of a gene of interest.

In an embodiment of the present disclosure, there is provided a method of obtaining a transgenic plant or parts thereof, including seeds, wherein said plant is male sterile, said method comprising: (a) obtaining a MS DNA construct as described herein; or a recombinant host cell comprising a MS DNA construct as described herein; (b) transforming plant cells with said MS DNA construct or said recombinant host cell to obtain transformed cells; and (c) selecting and regenerating transformed cells to obtain transgenic plant or parts thereof, including seeds, wherein said plant is male sterile.

In an embodiment of the present disclosure, there is provided a method of obtaining a transgenic plant or parts thereof, including seeds, wherein said plant is capable of restoring male sterility, said method comprising: (a) obtaining a RS DNA construct as described herein; or a recombinant host cell comprising a RS DNA construct as described herein; (b) transforming plant cells with said RS DNA construct or said recombinant host cell to obtain transformed cells; and (c) selecting and regenerating transformed cells to obtain transgenic plant or parts thereof, including seeds, wherein said plant is capable of restoring male sterility.

In an embodiment of the present disclosure, there is provided a method of obtaining a transgenic plant or parts thereof, including seeds, wherein said plant is capable of expression of a gene of interest, said method comprising: (a) obtaining a ES DNA construct as described herein; or a recombinant host cell comprising a ES DNA construct as described herein; (b) transforming plant cells with said ES DNA construct or said recombinant host cell to obtain transformed cells; and (c) selecting and regenerating transformed cells to obtain transgenic plant or parts thereof, including seeds, wherein said plant is capable of expression of a gene of interest.

In an embodiment of the present disclosure, there is provided a method of obtaining a transgenic plant or parts thereof, including seeds, wherein said plant is capable of inhibiting expression of a gene of interest, said method comprising: (a) obtaining a RS DNA construct as described herein; or a recombinant host cell comprising a RS DNA construct as described herein; (b) transforming plant cells with said RS DNA construct or said recombinant host cell to obtain transformed cells; and (c) selecting and regenerating transformed cells to obtain transgenic plant or parts thereof, including seeds, wherein said plant is capable of inhibiting expression of a gene of interest.

In an embodiment of the present disclosure, there is provided a method of obtaining a transgenic plant as described herein, wherein transformation of plant cells is carried out by any method known to a person skilled in the art.

In an embodiment of the present disclosure, there is provided a method of obtaining a transgenic plant as described herein, wherein transformation of plant cells is carried out by biolistic method.

In an embodiment of the present disclosure, there is provided a method of obtaining a transgenic plant as described herein, wherein transformation of plant cells is carried out by Agorbacterium mediated method.

In an embodiment of the present disclosure, there is provided a hybrid plant or parts thereof, including seeds comprising a MS DNA construct and a RS DNA construct.

In an embodiment of the present disclosure, there is provided a hybrid plant as described herein, wherein said MS DNA construct comprises: (a) a first expression cassette comprising a first tissue specific promoter operably linked to a desired gene of interest, expression of which leads to male sterility in plants, and a terminator; and (b) a second regulatory cassette comprising a second promoter operably linked to a fragment encoding a fusion peptide of N-terminal fragment of a transcription factor and TBPm3 having SEQ ID NO: 6, and a terminator.

In an embodiment of the present disclosure, there is provided a hybrid plant as described herein, wherein said RS DNA construct comprises an expression cassette comprising a third issue specific promoter operably linked to a restorer gene, and a terminator.

In an embodiment of the present disclosure, there is provided a hybrid plant as described herein, wherein said first tissue specific promoter is tapetum specific promoter TA29 having SEQ ID NO: 1.

In an embodiment of the present disclosure, there is provided a hybrid plant as described herein, wherein said desired gene of interest is selected from the group consisting of BARNASE, RNase, T-I, Mammalian uncoupling protein, Diptheria toxin A-chain, BAX, and AtBECLIN1.

In an embodiment of the present disclosure, there is provided a hybrid plant as described herein, wherein said desired gene of interest is AtBECLIN1 having SEQ ID NO: 2.

In an embodiment of the present disclosure, there is provided a hybrid plant as described herein, wherein said second promoter is constitutive or tissue specific.

In an embodiment of the present disclosure, there is provided a hybrid plant as described herein, wherein said second promoter is a constitutive promoter having SEQ ID NO: 4.

In an embodiment of the present disclosure, there is provided a hybrid plant as described herein, wherein said terminator is Nos terminator having SEQ ID NO: 3.

In an embodiment of the present disclosure, there is provided a hybrid plant as described herein, wherein said N-terminal fragment of a transcription factor is a 131 amino acid long fragment selected from the group consisting of HY5, HYH, and HFR1.

In an embodiment of the present disclosure, there is provided a hybrid plant as described herein, wherein said N-terminal fragment of a transcription factor is a 131 amino acid long fragment from HFR1.

In an embodiment of the present disclosure, there is provided a hybrid plant as described herein, wherein said third tissue specific promoter is tapetum specific promoter having SEQ ID NO: 7.

In an embodiment of the present disclosure, there is provided a hybrid plant as described herein, wherein said restorer gene is a mutant COP1 having SEQ ID NO: 8.

In an embodiment of the present disclosure, there is provided a hybrid plant as described herein, wherein said MS DNA construct comprises: (a) a first expression cassette comprising a first tapetum specific promoter TA29 having SEQ ID NO: 1 operably linked to AtBECLIN1 having SEQ ID NO: 2, expression of which leads to male sterility in plants, and a Nos terminator having SEQ ID NO: 3; and (b) a second regulatory cassette comprising a second constitutive promoter having SEQ ID NO: 4 operably linked to a fragment encoding a fusion peptide of 131 amino acid long fragment from HFR1 and TBPm3 having SEQ ID NO: 6, and a Nos terminator having SEQ ID NO: 3.

In an embodiment of the present disclosure, there is provided a hybrid plant as described herein, wherein said RS DNA construct comprises a third tapetum specific promoter having SEQ ID NO: 7 operably linked to a mutant COP1 having SEQ ID NO: 8, and a Nos terminator having SEQ ID NO: 3.

In an embodiment of the present disclosure, there is provided a hybrid plant or pars thereof, including seeds, comprising a MS DNA construct comprising: (a) a first expression cassette comprising a first tapetum specific promoter TA29 having SEQ ID NO: 1 operably linked to AtBECLIN1 having SEQ ID NO: 2, expression of which leads to male sterility in plants, and a Nos terminator having SEQ ID NO: 3; and (b) a second regulatory cassette comprising a second constitutive promoter having SEQ ID NO: 4 operably linked to a fragment encoding a fusion peptide of 131 amino acid long fragment from HFR1 and TBPm3 having SEQ ID NO: 6, and a Nos terminator having SEQ ID NO: 3; and a RS DNA construct comprising a third tapetum specific promoter having SEQ ID NO: 7 operably linked to a mutant COP1 having SEQ ID NO: 8, and a Nos terminator having SEQ ID NO: 3.

In an embodiment of the present disclosure, there is provided a method of obtaining a hybrid plant or parts thereof, including seeds, said method comprising: (a) obtaining a female of a male sterile transgenic plant as described herein; (b) obtaining a male of a transgenic plant capable of restoring male sterility as described herein; (c) crossing said female and male plant; (d) obtaining hybrid seeds from said female plant of step (c), which comprises a MS DNA construct as described herein and RS DNA construct as described herein, wherein in said seeds, male fertility is restored.

In an embodiment of the present disclosure, there is provided a method of obtaining a hybrid plant or parts thereof, including seeds, said method comprising: (a) obtaining a female of a male sterile transgenic plant as described herein; (b) obtaining a male of a transgenic plant capable of restoring male sterility as described herein; (c) crossing said female and male plant; (d) obtaining hybrid seeds from said female plant of step (c); and (e) developing said hybrid seeds into plants which comprise a MS DNA construct as described herein and RS DNA construct as described herein, wherein in said plants, male sterility is restored.

In an embodiment of the present disclosure, there is provided a method of switching off expression of a gene of interest in a F1 population of plants or parts thereof, including seeds, said method comprising: (a) obtaining a female of a transgenic plant comprising a ES DNA construct as described herein, wherein said plant is capable of expressing a gene of interest; (b) obtaining a male of a transgenic plant comprising a RS DNA construct as described herein, wherein said plant is capable of inhibiting expression of a gene of interest; (c) crossing said female and male plant; (d) obtaining hybrid seeds from said female plant of step (c), wherein said hybrid seeds comprise a ES DNA construct as described herein and RS DNA construct as described herein, and does not expression said gene of interest.

In an embodiment of the present disclosure, there is provided a method of switching off expression of a gene of interest in a F1 population of plants or parts thereof, including seeds, said method comprising: (a) obtaining a female of a transgenic plant comprising a ES DNA construct as described herein, wherein said plant is capable of expressing a gene of interest; (b) obtaining a male of a transgenic plant comprising a RS DNA construct as described herein, wherein said plant is capable of inhibiting expression of a gene of interest; (c) crossing said female and male plant; (d) obtaining hybrid seeds from said female plant of step (c); (d) developing said hybrid seeds into hybrid plants which comprise a ES DNA construct as described herein and RS DNA construct as described herein, and does not expression said gene of interest.

In an embodiment of the present disclosure, there is provided a MS DNA construct as described herein, for use in making transgenic plants.

In an embodiment of the present disclosure, there is provided a ES DNA construct as described herein, for use in making transgenic plants.

In an embodiment of the present disclosure, there is provided a RS DNA construct as described herein, for use in making transgenic plants.

In an embodiment of the present disclosure, there is provided a reversible expression system as described herein, for use in making transgenic plants.

Although the subject matter has been described in considerable detail with reference to certain preferred embodiments thereof, other embodiments are possible.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may vary.

Primer details, DNA sequence details, and further details of experiments as disclosed in the instant specification may be found in Singh, S. P. et. al., A novel male sterility-fertility restoration system in plants for hybrid seed production. Sci. Rep. 5, 11274; doi: 10.1038/srep11274 (2015).

Example 1

Isolation of a cDNA Encoding Beclin1 from *Arabidopsis*

*Arabidopsis thaliana* ecotype Columbia (Col-0) seedlings were taken and Total RNA was isolated by Plant spectrum Total RNA isolation kit (Sigma-aldrich). The quality of RNA was checked by visualizing the rRNA in ethedium bromide-coloured agarose gel under UV light. Twenty micrograms of total RNA was used in cDNA preparation using SuperScriprt™ Reverse Transcriptase kit (Invitrogen) following the manufacturer's instructions. The cDNA was used as template to amplify plant COP1 gene by using one set of primers, COP1_FP 5 'ccg ctc gag atg gaa gag att tcg acg gat cc3' (SEQ ID NO: 26) and COP1_RP 5'cga gct ctc acg cag cga gta cca gaa ctt 3' (SEQ ID NO: 27). The PCR reaction consisted of 30 cycles 94° C. for 30 sec, 58° C. for 30 sec and 72° C. for 120 sec. The PCR product of 2.0 kb was cloned in pBluescript SK+ vector (Stratagene, La Jolla, Calif.). Nucleotide sequence of the cloned PCR product was determined by using Big Dye Terminator v3.1 Cycle Sequencing Kit (Applied Biosystems). Sequence homology was analyzed using BLAST program.

Example 2

Isolation of a cDNA Encoding COP1 from *Arabidopsis*

*Arabidopsis thaliana* ecotype Columbia (Col-0) seedlings were taken and Total RNA was isolated by Plant spectrum Total RNA isolation kit (Sigma-aldrich). The quality of RNA was checked by visualizing the rRNA in ethedium bromide-coloured agarose gel under UV light. Twenty micrograms of total RNA was used in cDNA preparation using SuperScript™ Reverse Transcriptase kit (Invitrogen) following the manufacturer's instructions. The cDNA was used as template to amplify plant COP1 gene by using one set of primers, COP1_FP 5'ccg ctc gag atg gaa gag att tcg acg gat cc3' and COP1 RP 5'cga gct etc acg cag cga gta cca gaa ctt 3'. The PCR reaction consisted of 30 cycles 94° C. for 30 sec, 58° C. for 30 sec and 72° C. for 120 sec. The PCR product of 2.0 kb was cloned in pBluescript SK+ vector (Stratagene, La Jolla, Calif.). Nucleotide sequence of the cloned PCR product was determined by using Big Dye Terminator v3.1 Cycle Sequencing Kit (Applied Biosystems). Sequence homology was analyzed using BLAST program.

Example 3

Site Directed Mutagenesis in COP1 to Form COP1$^{L105A}$

Site directed mutagenesis PCR was performed using QuikChange XL Kit (Stratagene) according to the manufacture's instruction. 5"1"TTCGCGGCCGA-TAAGGCAGCGAAG 3' (SEQ ID NO: 10) mutation was introduced in the 5' TTCTTGCTCGATAAGCTATTGAAG 3' (SEQ ID NO: 11) region of COP1 gene by using two set of primers COPM_f1 5'GCT TTA CCC TAA TTT CGC GGC CCG ATA AGC TAT TGA AGA AAA CTT C 3' (SEQ ID NO: 12), COPM_ r1 5'GTT TTC TTC AAT AGC TTA TCG GCC_GCG AAA TTA GGG TAA AGC TG 3' (SEQ ID NO: 13) and COPM_f2 5' TAA TTT CTT GCT CGA TAA GGC AGC GAA GAA AAC TTC AGC TCG GC 3' (SEQ ID NO: 14), COPM_r2 5' CGA GCT GAA GTT TTC TTC GCT GCC TTA TCG AGC AAG AAA TTA GG 3' (SEQ ID NO: 15) primers, Clones were screened by DNA sequencing for the desired mutation using T3 and T7 primers.

Example 4

Isolation of a cDNA Encoding HFR1$_{n-131}$ from *Arabidopsis*

*Arabidopsis thaliana* ecotype Columbia (Col-0) seedlings were taken and Total RNA was isolated by Plant spectrum Total RNA isolation kit (Sigma-aldrich), The quality of RNA was checked by visualizing the rRNA in ethedium bromide-coloured agarose gel under UV light. Twenty micrograms of total RNA was used in cDNA preparation using SuperScript™ Reverse Transcriptase kit (Invitrogen) following the manufacturer's instructions. The cDNA was used as template to amplify only 131 amino acid N-terminus fragment of plant HFR1 coding gene by using one set of primers, HfrI_F1 5'cca tcg ata tgt cga ata atc aag ctt tca tgg 3 '(SEQ ID NO. 28) and 5'cca tcg att ctt gta aac tcc tcc gat tca tc3' (SEQ ID NO: 29). The PCR reaction consisted of 30 cycles 94° C. for 30 sec, 58° C. for 30 sec and 72° C. for 30 sec. The PCR product of 0.4 kb was cloned in pBluescript SK+ vector (Stratagene, La Jolla, Calif.). Nucleotide sequence of the cloned PCR product was determined by using Big Dye Terminator v3,1 Cycle Sequencing Kit (Applied Biosystems). Sequence homology was analyzed using BLAST program.

Example 5

Construction of Chimeric Gene Fusions

Construction of expression module (em), Construct 1 (FIG. 1A): An early stage, tapetum specific 1 kb BamH1/Xba1 promoter was fused with 1.8 kb Xba1/Sac1 gusA gene and 250 bp Sac1/EcoR1 Nos terminator in BamH1/EcoR1 Sk+ Cloning vector. In second Sk+ Cloning vector 0.4 kb SalI/ClaI promoter Pcec was fused with 0.4 kb ClaI/ClaI HFR1$^{n-131}$ and 0.6 kb ClaI/SacI TBPm3 genes and 250 bp Sac1/EcoR1 Nos terminator in Sal1/EcoR1 Sk+ Cloning vector. First expression fragment (TA29(m):gusA:Tnos) was isolated with BamH1/SalI site and second fragment (Pcec:HFR1$^{n-131}$:TBPm3:Tnos) with SalI/EcoRI were triple ligated into BamH1/EcoRI cleaved binary vector pBI101. The resultant pBI101 carrying the expression cassette was transformed into *Agrobacterium tumefaciens* strain LBA4404 following the modified protocol (Cangelosi et al., 1991).

Construction of Male sterility module (ms), Construct 2 (FIG. 1B): An early stage, tapetum specific 1 kb BamH1/Xba1 promoter was fused with 1.5 kb Xba1/Sac1 Beclin1 gene and 250 bp Sac1/EcoR1 Nos terminator in BamH1/EcoR1 Sk+ Cloning vector. In second Sk+ Cloning vector 0.4 kb SalI/ClaI promoter Pcec was fused with 0.4 kb ClaI/ClaI HFR1$^{n-131}$ and 0.6 kb ClaI/SacI TBPm3 genes and 250 bp Sac1/EcoR1 Nos terminator in Sal1/EcoR1 Sk+ Cloning vector. First expression fragment (TA29(m):Beclin1:Tnos) was isolated with BamH1/SalI site and second fragment (Pcec:HFR1$^{n-131}$:TBPm3:Tnos) with SalI/EcoRI were triple ligated into BamH1/EcoRI cleaved binary vector pBI101. The resultant pBI101 carrying the expression cassette was into *Agrobacterium tumefaciens* strain LBA4404 following the modified protocol (Cangelosi et al., 1991).

Construction of restoration module (rs), Construct 3(FIG. 1C): *Arabidopsis* tapetum specific promoter A9 1.5 kb SalI/ClaI was fused with 2.0 kb ClaI/SacI plant COP1$^{L105A}$ gene and 250 bp Sac1/EcoRI Nos terminator in SalI/EcoRI Sk+ Cloning vector. pCAMBIA1300 binary vector was modified by replacing CaMV35S promoter by XhoI/BstXI Pnos promoter. The expression cassette (A9: COP1L105A: Tnos) SalI/EcoRI was subcloned in binary vector Modified pCAMBIA1300 SalI/EcoRI. The resultant pBI101 carrying the expression cassette was into *Agrobacterium tumefaciens* strain LBA4404 following the modified protocol (Cangelosi et al., 1991).

Example 6

Transformation of Tobacco Plants

As described in Example 4, recombinant *Agrobacterium tumefaciens* carrying the expression cassette was used for transformation of *Nicotina tabacum* cv. *Petit Havana* by protocol as described by Horsch et al., in 1985.

In short a single isolated colony of *A. tumefaciens* LBA 4404 harboring binary vector with above described expression cassettes was inoculated in YEP medium containing antibiotics streptomycin (250 µg/ml) rifampicin (50 µg/ml) and kanamycin (100 µg/ml) and grown (200 rpm, overnight, 28° C.). Fifty micro liters of the overnight culture was diluted to 100 ml in YEP medium and grown till OD$_{600}$ reached to 0.8. Cells were recovered by centrifugation in SS34 rotor (5,000 rpm, 10 min, 4° C.). The pellet was suspended in co-cultivation medium (MS salts, 2% glucose, 10 mM MES and 100 mM acetosyrengone, pH 5.6) to OD$_{600}$ 0.6. Tobacco leaf discs were co-cultivated with *A. tumefaciens* for two days in dark. After co-cultivation, the leaf discs were transferred to regeneration medium supplemented with cefotaxime (250 µg/ml) and kanamycin (100 µg/ml). The culture was incubated at 25 with 16 hrs light and 8 hrs dark cycle for a period of four weeks. After this, the transgenic shoots were harvested and transferred to rooting medium containing kanamycin (50 µg/ml). After incubation for 2-4 weeks, the putative transgenic plantlets were transferred to Hoagland solution for acclimatization and then transferred to vermiculite for hardening for three weeks. The plants were transferred from vermiculite to soil in glasshouse. Independent transgenic lines were developed for the expression cassette (chimeric gene fusion).

The same method was deployed for all three constructs.

Example 7

Analysis of Transgenic Lines for Transgene Integration

Genomic DNA of the transgenic lines and control plant was isolated by CTAB method of DNA extraction.

Analysis of transgenics; The genomic DNA was used as template to amplify a fragment of 2.5 kb comprising TA29 promoter and plant Beclin 1 gene by using one set of primers, 5'cgc gga tcc aga tct tcc aac att tact cc aag gg 3' (SEQ ID NO: 30) and 5'cgt cga gct cct aag ttt ttt tac atg aag gct ta 3' (SEQ ID NO: 31). The PCR reaction consisted of 94° C.; for 4 min, 94° C. for 1 min, 60° C. for 1 min and 72° C. for 2 min, Go to 2 for 30 cycles 72° C. for 5 min. The desired band of 2.5 kb was obtained in the PCR of transgenic lines and positive control but not in control plants and negative control (without template). This experiment was repeated for three times for conformation.

Analysis of es transgenics; The genomic DNA was used as template to amplify a fragment of 1.67kb using Pcec_FP 5 '-AAGGGCCTCGGTAATACCATTG-3 (SEQ ID NO: 16) and Tnos_RP 5'-CCATCGATCTAGTAACATA-GATGACAC-3 (SEQ ID NO: 7'. The PCR reaction consisted of 94° C. for 4 min, 94° C. for 1 min, 58° C. for 2 min and 72° C. for 2 min. Go to 2 for 30 cycles 72° C. for 5 min. The desired band of 1.67kb was obtained in the PCR of transgenic lines and positive control but not in control plants and negative control (without template). This experiment was repeated for three times for conformation.

Analysis of rs transgenics; The genomic DNA was used as template to amplify a fragment of 3.5kb using A9_FP 5'-ACGCGTCGACTCTAGACATAAGGTGAGAGTTAA-3'(SEQ ID NO: 18) and COP9 RP 5'CGAGCTCT-CACGCAGCGAGTACCAGAACTT-3' (SEQ II) NO: 19). The PCR reaction consisted of 94° C. for 4 min, 94° C. for 1 min, 61° C. for 1 min and 72° C. for 3 min, Go to 2 for 30 cycles 72° C. for 5 min. The desired band of 3.5kb was obtained in the PCR of transgenic lines and positive control but not in control plants and negative control (without template). This experiment was repeated for three times for conformation.

Example 8

Analysis of Expression Module (es) Transgenic

Transgenic of expression module (TA$_{29}$ (TGTA)-gusA-Tnos-Pcec-HFR1$^{n-131}$-TBPm3-Tnos) was analyzing at maturity.

Fluorometric GUS assay; The anthers of developmental stage 3 and stage 4 were collected and florimetric GUS assay was performed. The anthers of one flower bud (16-20 mg) were crushed in liquid nitrogen, suspended in 0.180 ml of GUS extraction buffer (50 mM Na$_2$HPO$_4$ pH-7.0, 10 mM DTT, 1 mM EDTA, 0.1% SLS, 0.1% Triton X-100) and transferred to 1.5 ml eppendorf tubes. Whole procedure here after was done at 4° C. Cellular debris was pelleted by centrifugating the samples at 13,000 rpm for 20 min, and the supernatant were transferred into fresh tubes. 9 µl of extract was mixed with 1 µl of 10×GUS assay buffer (MUG suspended in GUS extraction buffer) in fresh tubes and mixed by pipeting. The tubes were covered to protect from light and incubated at 37° C. for 1 h. After the incubation period the reaction was stopped by adding 90 µl of 0.2 M sodium carbonate solution. The tubes were mixed properly by vortexing for few seconds. Relative fluorescence of MU was recorded using Perkin Elmer Spectrofluorometer with an excitation at 365 nm and emission at 455 nm. Total soluble protein in anther extract was quantified, using the Bio-Rad dye.

Histochemical GUS analysis; The anther of developmental stage 3 was collected and histochemical GUS analysis was performed. Whole anthers of stage 3 were placed in a 50 mM 5-bromo-4-chloro-3-indolylglucuronide (X-Gluc) solution (50 mM sodium phosphate buffer pH7, 0.2% Triton X100, 3 mM potassium ferricyanide, 3 mM potassium ferrocyanide, 20% methanol) and vacuum infiltrated at 200 mm Hg for 5 minute, three times with the interval of 15 minutes. Then incubate for overnight. Stained anthers were fixed overnight in 4% paraformaldehyde Fixative at 4° C. Fixed anthers were dehydrated in ethanol series 50%, 70%, 85%, 95% and 100% for 1 h each. Infiltration was done in 2:1, 1:1 and 1:0 of (ethanol: infiltration solution) for 1 h each and embedded in resin (JB-4 Embedding Kit, Polysciences Inc. Eppelheim, Germany). 12-µM thick sections were cut using Leica microtome and pictures were captured using Leica microscope.

Crossing; ES transgenic were crossed with RS (ES(♀) xRS(♂)). The resultant F1 seeds were collected and sown on kanamycin (100 µg/ml) and hygromycin (50 µg/ml). Germinated seedlings were transferred on the soil to raise F1 plants.

F1 analysis; The anther of stage 3 and stage 4 were collected and histochemical and fluoremertric gus assay was performed as described above. Leaf, root, bud and stem were also taken for the analysis to check the specificity of the expression to anther tapetum.

Example 9

Analysis of Transgenic (MS) for Male Sterility and Restored Fertility of F1 Hybrid The transgenic plants grew well to visible maturity and showed normal flowering. Expression of the autophagy gene in anthers did not lead any morphological abnormalities except nonviable pollens and defected seed setting.

Pollen viability assay was performed using double stain Fluorescein diacetate (FDA) and propedium iodide (PI). 2 mg/ml FDA solution was made in acetone in darkness. 10% sucrose solution was added drop by drop until FDA solution turn milky. PI of 1 mg/ml in final volume was added in the working FDA. Pollen from Control (NTPH), 1370 transgenic lines and F1 lines (1370(♀)×1373(♂)) were incubated in for 5 min. followed by 3 washes in PBS. Pollens were collected by centrifuge and mounted on slowfade antifade (invitrogen) and observed under confocal microscope (LSM510META, CarlZeiss) using FDA (excitation 495 emission 519) and PI (excitation 536 emission 617). Viable pollen stained with FDA while aborted pollen was stained with PI. % of pollen viability was calculated by counting FDA/PI stained pollen in unit area (n=10).

Pollen germination assay; In vitro pollen germination test was performed by using a liquid medium consisting of 10% Sucrose, 0.1 mg/ml Boric acid, 0.3 mg/ml Calcium nitrate, 0.2 mg/ml Magnesium sulphate, 0.1 mg/ml Potassium nitrate (Kwack, 1964). A droplet of pollen germination medium was deposited over pollen sample on a slide. The slide was placed in a petriplate over folded foil in such a position that the droplet along with pollen should hang. A wet filter paper was placed at the base of the petriplate to maintain some humidity around the germinating pollen. Data of pollen germination was recorded after 6 hours.

Seed setting was observed after bagging the inflorescence before anthesis of flowers.

Example 10

Real Time PCR Analysis

Different developmental stages (S1-S6) of anther of MS, RS and F1 plants were taken and Total RNA was isolated by Plant spectrum Total RNA isolation kit (Sigma aldrich). The quality of RNA was checked by visualizing the rRNA in ethedium bromide-coloured agarose gel under UV light. Two micrograms of total RNA was used in cDNA preparation using SuperScript™ Reverse Transcriptase kit (Invitrogen) following the manufacturer's instructions. qRT-PCR of COP1 was performed by using primer COP1RT_F 5' AAGCGGCGGTTCTGAGATT3' (SEQ ID NO: 20) COP1R 5'ACCACAAGCCGTGAGGAAAG3' (SEQ ID NO: 20 and BECLIN1 by using AtBECLIN 1 forward 5'AGGGCATTCCTCCACGTC3' (SEQ ID NO: 22) and reverse primer 5' AAGAGACA GATTGTGAGAAC-CACCA 3' (SEQ ID NO: 23) on AB I prism 7700 sequence detection system (Applied Biosystem, Foster city, CA, USA, http://www.appliedbiosystems.com). The AtBECLIN1 transcript was normalized with respect to ubiquitin transcript as internal control. For ubiquitin, primers (UbiF) 5'CCACG-GAGACGGAGGACAA3'(SEQ ID NO: 24) and (UbiR) 5'GAAGCA GCTCGAGGATGGAA 3'(SEQ ID NO: 25) were used. The real time PCR mixture with reaction volume 20 µl contained 10 µl of Sybr green master mix, 1 µl cDNA and 5 pmoles each of primers.

SEQUENCE LISTING

<110> Council of Scientific and Industrial Research

<120> Novel reversible expression system for transgene expression in plants

<130> NA

<160> 9

<170> PatentIn version 3.5

<210> 1
<211> 1021
<212> DNA
<213> Nicotiana tabacum

<400> 1

```
cgcggatcca gatcttccaa caccatttac tccaagggca ctgtagtaaa aaaataatta        60
aatcattttt gaaatctaaa aaactcactt attttggacc ataaaaaaag ggccaaaaaa       120
taacttattg tggaccggag agagtaatac acttttttggt tagcgaatgc aattaattta      180
gacattgtgt tatgttccag ttaaccgctt ccctgcactt ctttcaatct atctctcgat       240
agaaaattgt gatactttgc gacttctatc agaggacttt tgttttcca tgtaacaatc        300
tgtcattttc gatggggaga tttgcacaaa taggctattt atgtgtccca atttaaattt       360
taacccatg tcgatcagaa cttagccacg agcaccagaa gtttgatgga tatgtgactt        420
tgtcactatc cggtttacta atcaagagct attttattc aaaattggat atctagctaa        480
gtataactgg ataatttgca ttaacagatt gaatatagtg ccaaacaaga agggacaatt      540
gacttgtcac tttatgaaag atgattcaaa catgattttt tatgtactaa catatacatc       600
ctactcgaat taaagcgaca taggctcgaa gtatgcacat ttagcaatgt aaattaaatc       660
agttttttgaa tcaagctaaa agcagacttg cataaggtgg gtggctggac tagaataaac     720
atcttctcta gcacagcttc ataatgtaat ttccataact gaaatcaggg tgagacaaaa       780
ttttggtact ttttcctcac actaagtcca tgtttgcaac aaattaatac atgaaaccttt     840
aatgttaccc tcagattagc ctgctactcc ccattttcct cgaaatgctc caacaaaagt       900
tagttttgca agttgttgtg tatgtcttgt gctctatata tgcccttgtg gtgcaagtgt       960
aacagtacaa catcatcact caaatcaaag tttttactta agaaattag ctaaatctag       1020
a                                                                    1021
```

<210> 2
<211> 1554
<212> DNA
<213> Arabidopsis thaliana

<400> 2

```
atgaggaaag aggagattcc agataaaagt cggactatcc cgatcgatcc gaatctgccg        60
aaatgggtct gccaaaactg tcaccactcc cttaccatcg tcggcgtcga ttcctacgcc       120
ggcaagttct tcaacgatcc ccctccgtcc gctacgcagg gctcatctat ccatggagct       180
aacagtgttc ttggttcaac acgcatggac aactcttttg ttgttttacc tcgacataag       240
cctcctcaat ctcagggcat tcctccacgt cctcgcgggg cgtcctcacc tcagcctgat       300
gctactcaat ctggaaaggc gatggaggaa tcgtttgtag ttgtctataa gtctgagcct       360
```

SEQUENCE LISTING

```
gtttctgatt ctggtggttc tcacaatctg tctcttgaag tgggccaaaa cggtcccttt       420
cattcaaata cttctggctt taatgcgact atcaatgtct taactcgtgc ttttgatatt       480
gctagaactc agacacaggt tgaacagcca ttgtgcttag aatgcatgag ggtattgtct       540
gataaacttg aaaagaagt cgaggatgtg acgagggacg tggaagcata cgaagcatgc        600
gttcagaggt tagaaggaga gacgcaagat gttcttagtg aagctgattt tctcaaggaa       660
aagaagaaga ttgaggaaga agaaagaaaa cttgttgcag ctatagaaga aacagagaaa       720
caaaatgctg aagtaaacca tcaactgaag gagctagaat tcaagggaaa tcgttttaac       780
gaacttgaag atcggtattg gcaagagttc aataattttc agtttcaatt aattgcccat       840
caggaagaga gagatgcaat cttggcaaag attgaagttt cacaagcaca tttagagtta       900
ttaaataaga caaatgtact tattgatgcc ttccccatac ggaatgatgg ggaatttggt       960
acaattaaca attttcgact tggaagactc cctgccataa aagttgagtg ggatgagatc      1020
aatgctgctt ggggccaagc ctgtcttctc ctccatacga tgtgtaacta tttccggcca      1080
aagtttcaat gtcaagttaa aatacagccg atggggagtt atcctagaat tgtagacagc      1140
aacaacgaaa cttatgagct gttttggtcct gttaacttgt tttggagcac tcggtacgat      1200
aaagccatga cactgtattt gatgtgtctt aaagactttg ctgattttgc aaattcaaag      1260
gaccaagaga acaatattcc accagataat tgcctcaacc ttccatacaa gatcgaaaag      1320
gacaaagtat tggggtattc aataacacag agcttcaaca agcaagagag ttggaccaaa      1380
gcactaaagt atactctctg caacctcaaa tgggctctct actggttcgt tggaaacact      1440
aatttccaac ctctctctgc gacggtctct ctgccttcta atatatcagc ggctggttcc      1500
ttgtacgcca agcgaggtcc tgactctagt aagccttcat gtaaaaaaac ttag           1554
<210>     3
<211>     277
<212>     DNA
<213>     plasmid
<400>     3
gagctcgaat tcccccgatc gttcaaacat ttggcaataa agtttcttaa gattgaatcc        60
tgttgccggt cttgcgatga ttatcatata atttctgttg aattacgtta agcatgtaat       120
aattaacatg taatgcatga cgttatttat gagatgggtt tttatgatta gagtcccgca       180
attatacatt taatacgcga tagaaaacaa atatagcgc gcaaactagg ataaattatc        240
gcgcgcggtg tcatctatgt tactagatcg ggaattc                                277
<210>     4
<211>     450
<212>     DNA
<213>     Promoter
<400>     4
gtcgaccatc atttgaaagg gcctcggtaa taccattgtg gaaaaagttg gtaatacgga        60
aaaagaagat tcatcatcca gaaaggtgt ggaaaagttg tggattgcgt ggaaaaagtt       120
cgatctgacc atctctagat cgtggaaaaa gttcacgtaa gcgcttacgt acatatgtgg      180
attgtggaaa aagaagacgg aggcatcggt ggaaaaagaa gcttgtacgc tgtacgctga      240
```

-continued

SEQUENCE LISTING

```
cgatagatag atacacgtgc acgcgtccac ttgacgcaca attgacgcac aatgacgcca      300
cttgacgcta cttcactata tataggaagt tcatttcatt tggaatggac acgtgttgtc      360
atttctcaac aattaccaac aacaacaaac aacaaacaac attatacaat tactatttac      420
aattacatct agataaacaa tggcttcctc                                       450
```

<210> 5
<211> 393
<212> DNA
<213> Arabidopsis thaliana
<400> 5

```
atgtcgaata atcaagcttt catggaattg ggatggagaa acgacgtcgg atcacttgct       60
gtgaaagatc agggcatgat gtcagaaaga gcaagaagtg atgaagatcg tctaatcaac      120
ggtctaaaat ggggctacgg ctactttgat catgatcaaa ctgataatta tcttcagatt      180
gttccagaga ttcataaaga agtagaaaat gcgaaggagg attattggt tgttgtccct       240 gatgaacatt ctgaaactga tgatcatcat catattaaag atttttcaga gagatcagat      300
catcgatttt atctgagaaa caaacatgag aaccccaaaa aacgtcgtat ccaggtctta      360
agtagtgatg atgaatcgga ggagtttaca aga                                   393
```

<210> 6
<211> 603
<212> DNA
<213> Arabidopsis thaliana
<400> 6

```
atgactgatc aaggattgga agggagtaat ccagttgatc ttagcaagca tccttcaggg       60
attgttccta ctcttcaaaa cattgtctcc acggtgaact agactgcaa gctagatctt       120 aaagccatag ctttgcaggc tcggaatgct gaatataatc ccaagcgttt tgctgcggtg      180
ataatgagga tcagagaacc gaagactaca gcattaatat tcgcctcagg gaaaatggtc      240
tgtactggag ctaagagcga ggacttttcg aagatggctg ctagaaagta tgctaggatt      300
gtgcagaaat tgggattccc tgcaaaattc aaggatttca agattcagaa tattgtaggt      360
tcttgtgatg tcaaattccc tataagactt gaaggtcttg cttactctca cgctgctttc      420
tcaagttatg agcccgagct cttcccaggg ctgttttata ggatgaaagt cccaaaaatc      480
acccttgtaa tctttgtctc tgggaagatc gtaataacag gagccaagat gagagatgag      540
acctacaaag cctttgagaa tatataccc gtgctctcgg aattcagaaa gatacagcaa      600
tag                                                                    603
```

<210> 7
<211> 1952
<212> DNA
<213> Arabidopsis thaliana
<400> 7

```
tctagacata acggtgagag ttaatattaa aatttcaggc gagaaaaatg atacttgaaa       60
```

-continued

| SEQUENCE LISTING | |
|---|---|
| aatattatga tcgttttgga tattccttac atcgagtgaa tgttggtttg attcatcttc | 120 |
| caagtgttct gcaaacgtat attaaaggtt tattaactgg taagagatta accgggtttt | 180 |
| ggttcagcat ataccatgat tgactaactg atcaaatagt ctttacttat tatataaaga | 240 |
| cgatactatt ggtcatgcta caaaatcaag tcataccata tcctgagaat gaatgtggag | 300 |
| aatcgttata aggcataagt gtgggtattg atcgtggtac gaacaaccgc cttggcatca | 360 |
| acattagcca cgatatccaa catttgaagc attgcctatg gcgagtgttt ggttggtttt | 420 |
| gaaactgatg atgataacca gaacgagaaa tgtcttgtga agtataatgt tccgatgaat | 480 |
| tgggattata ataatgtgta gacattgtag gttggttttg atgatgataa gtaatcattg | 540 |
| gagaattgtc taacacatgc actggagaat tattgactct accacgttct ctttgatatt | 600 |
| cctcgatttt cctcgtgatt tcatcagcct ctccgaaaaa gtaattgtat ccactagaac | 660 |
| tttgggaatc tcccatctaa tttatgtatt agagaagtta taatattttg gggaaataga | 720 |
| ttttctctac tgatttttgtt gtgtgacatt atatttttat aagtacatgt ttctgtttcg | 780 |
| ttatattgtt gtcgtggttg agtctttatt agagcatgta aatatgttta tgaaataagc | 840 |
| gagaaaggaa ttaattaaac gtatcgagtg ataaatgctt taatggattc gagatttagt | 900 |
| attcttaaat ttttgtttca ttatcattga ttataaaact aagttatgtt gatctcaaat | 960 |
| ccttaattat gttctcctaa gaagagtaca agtggtggga acgaaagatg agtaaaatac | 1020 |
| taaaatctt ttctcaaaag tcaaatcgca ttagttaaca aaaacaaacc atgtgttacc | 1080 |
| gtcaaatcaa tgtgtttaaa agatgttaac cactaatcaa gcatttacgt gtaaccggat | 1140 |
| caaccggatt tgggttttga atatgttgtg gagatgtata taaatgataa attaattgaa | 1200 |
| tatcttaatt aatctgtgaa agaaactaca tcacacactt tgttatttcc cctagctttt | 1260 |
| agttttttta tcatgcaaaa cttatgaagt aactagatca agatcacaaa aaaaaagcat | 1320 |
| cacttcactt catgacctaa ttattctcga agcccaaaac tatttacata cacttttatt | 1380 |
| ctataaatat agatgatgga attcaccaat ccaaagtgaa ataaaaaaca caagtacaaa | 1440 |
| caatatagta tctaattaga atggtatctc taaagtccct tgctgctatt ctcgttgcca | 1500 |
| tgtttcttgc caccggacct acggttctag cccagcagtg cagagacgaa ctgagcaatg | 1560 |
| tgcaggtgtg cgcgccgctg cttctgcccg gtgcggtcaa tcctgccgcg aactcaaatt | 1620 |
| gctgcgctgc cctccaagca actaacaaag attgtctatg taaccgtctt cgagcagcca | 1680 |
| ccacacttac ctctctttgt aacctcccct cttttgattg tggtaagatg atccatcgat | 1740 |
| taaaaccttt tttactagat ttttataaat tattccatca atagtgtttg ttttatattt | 1800 |
| gttctcatga tttttggac ttatgttttg tgaactgtgc aggcataagt gcctagttga | 1860 |
| acaacattca gttccgagga tttggggagt ttggtctgca aacgacaaga cgaataaaat | 1920 |
| aaaataatga gaaatacact atttagtgtt tt | 1952 |
| <210> 8 | |
| <211> 2007 | |
| <212> DNA | |
| <213> Arabidopsis thaliana | |
| <400> 8 | |
| atggaagaga tttcgacgga tccggttgtt ccagcggtga aacctgaccc gagaacatct | 60 |
| tcagttggtg aaggtgctaa tcgtcatgaa aatgacgacg gaggaagcgg cggttctgag | 120 |

SEQUENCE LISTING

```
attggagcac cggatctgga taaagacttg ctttgtccga tttgtatgca gattattaaa      180
gatgctttcc tcacggcttg tggtcatagt ttctgctata tgtgtatcat cacacatctt      240
aggaacaaga gtgattgtcc ctgttgtagc caacacctca ccaataatca gctttaccct      300
aatttcttgc tcgataagct attgaagaaa acttcagctc ggcatgtgtc aaaaactgca      360
tcgcccttgg atcagtttcg ggaagcacta caaaggggtt gtgatgtgtc aattaaggag      420
gttgataatc ttctgacact tcttgcggaa aggaagagaa aaatggaaca ggaagaagct      480
gagaggaaca tgcagatact tttggacttt ttgcattgtc taaggaagca aaaagttgat      540
gaactaaatg aggtgcaaac tgatctccag tatattaaag aagatataaa tgccgttgag      600
agacatagaa tagatttata ccgagctagg gacagatatt ctgtaaagtt gcggatgctc      660
ggagatgatc caagcacaag aaatgcatgg ccacatgaga agaaccagat tggtttcaac      720
tccaattctc tcagcataag aggaggaaat tttgtaggca attatcaaaa caaaaaggta      780
gaggggaagg cacaaggaag ctctcatggg ctaccaaaga aggatgcgct gagtgggtca      840
gattcgcaaa gtttgaatca gtcaactgtc tcaatggcta gaaagaaacg gattcatgct      900
cagttcaatg atttacaaga atgttacctc caaaagcggc gtcagttggc agaccaacca      960
aatagtaaac aagaaaatga taagagtgta gtacggaggg aaggctatag caacggcctt     1020
gcagattttc aatctgtgtt gactaccttc actcgctaca gtcgtctaag agttatagca     1080
gaaatccggc atggggatat atttcattca gccaacattg tatcaagcat agagtttgat     1140
cgtgatgatg agctgtttgc cactgctggt gtttctagat gtataaaggt ttttgacttc     1200
tcttcggttg taaatgaacc agcagatatg cagtgtccga ttgtggagat gtcaactcgg     1260
tctaaactta gttgcttgag ttggaataag catgaaaaaa atcacatagc aagcagtgat     1320
tatgaaggaa tagtaacagt gtgggatgta actactaggc agagtcttat ggagtatgaa     1380
gagcacgaaa aacgtgcctg gagtgttgac ttttcacgaa cagaaccatc aatgcttgta     1440
tctggtagtg acgactgcaa ggttaaagtt tggtgcacga ggcaggaagc aagtgtgatt     1500
aatattgata tgaaagcaaa catatgttgt gtcaagtaca atcctggctc aagcaactac     1560
attgcggtcg gatcagctga tcatcacatc cattattacg atctaagaaa cataagccaa     1620
ccacttcatg tcttcagtgg acacaagaaa gcagtttcct atgttaaatt tttgtccaac     1680
aacgagctcg cttctgcgtc cacagatagc acactacgct tatgggatgt caaagacaac     1740
ttgccagttc gaacattcag aggacatact aacgagaaga actttgtggg tctcacagtg     1800
aacagcgagt atctcgcctg tggaagcgag acaaacgaag tatatgtata tcacaaggaa     1860
atcacgagac ccgtgacatc gcacagattt ggatcgccag acatggacga tgcagaggaa     1920
gaggcaggtt cctactttat tagtgcggtt tgctggaaga gtgatagtcc cacgatgttg     1980
actgcgaata gtcaaggaac catcaaa                                         2007
```

<210> 9

<211> 307

<212> DNA

<213> plasmid

<400> 9

```
gatcatgagc ggagaattaa gggagtcacg ttatgacccc cgccgatgac gcgggacaag       60
```

SEQUENCE LISTING

```
ccgttttacg tttggaactg acagaaccgc aacgttgaag gagccactca gccgcgggtt    120
tctggagttt aatgagctaa gcacatacgt cagaaaccat tattgcgcgt tcaaaagtcg    180
cctaaggtca ctatcagcta gcaaatattt cttgtcaaaa atgctccact gacgttccat    240
aaattcccct cggtatccaa ttagagtctc atattcactc tcaatccaaa taatctgcac    300
cggatct                                                              307
```

<210> 38
<211> 21
<212> DNA
<213> *Propionibacterium acnes*

<400> 38

```
ccggtattag ccccagtttc c                                               21
```

<210> 39
<211> 19
<212> DNA
<213> Gram -ve bacterial specific portion of gyr B gene
<400> 39

```
cggcggcaag ttcgacgac                                                  19
```

<210> 40
<211> 19
<212> DNA
<213> Gram -ve bacterial specific portion of gyr B gene
<400> 40

```
ccaccgagac gcccacacc                                                  19
```

<210> 41
<211> 18
<212> DNA
<213> Gram -ve bacterial aconitate hydratase gene
<400> 41

```
ccaggtcggc ggagaagc                                                   18
```

<210> 42
<211> 17
<212> DNA
<213> Gram -ve bacterial aconitate hydratase gene
<400> 42

```
ccaccggccc gatgacc                                                    17
```

<210> 43
<211> 18
<212> DNA
<213> Gram -ve ribonuclease 1 gene

SEQUENCE LISTING

```
<400>  43 gccgccctga ccaccttc                                            18

<210>  44
<211>  19
<212>  DNA
<213>  Gram -ve ribonuclease 1 gene

<400>  44 gcgggttgtt cggcatcag                                           19

<210>  45
<211>  87
<212>  DNA
<213>  Herpes simplex virus

<400>  45 cgcttggttt cggatgggag gcaactgtgc tatccccatc acggtcatgg agtacaccga    60
atgctcctac aacaagtctc tgggggc                                  87

<210>  46
<211>  70
<212>  DNA
<213>  Herpes simplex virus

<400>  46 ggcaatcgtg tacgtcgtcc gcacatcaca gtcgcggcag cgtcatcggc ggtaacgcaa    60
gacccccccg                                                     70

<210>  47
<211>  79
<212>  DNA
<213>  Herpes simplex virus

<400>  47 caagctgacg gacatttaca aggtcccccct ggacgggtac ggccgcatga acggccgggg    60
cgtgtttcgc gtgtgggac                                           79

<210>  48
<211>  72
<212>  DNA
<213>  Cytomegalovirus

<400>  48 ttccggctca tggcgttaac caggtagaaa ctgtgtgtac agttgcgttg tgcgtaacgt    60
aaaagcaggg cg                                                  72

<210>  49
<211>  65
```

SEQUENCE LISTING

<210> 49

<211> 65

<212> DNA

<213> Cytomegalovirus

<400> 49

```
cggcgacgac gacgataaag aatacaaagc cgcagtgtcg tccagaggat tacgcgacca    60
gattg                                                                65
```

<210> 50

<211> 68

<212> DNA

<213> Cytomegalovirus

<400> 50

```
gggcacgtcc tcgcagaagg actccaggta caccttgacg tactggtcac ctatcacctg    60
catcttgg                                                             68
```

<210> 51

<211> 79

<212> DNA

<213> Varicella zoster

<400> 51

```
ggtcttgccg gagctggtat taccttaaaa ctcactacca gtcatttcta tccatctgtc    60
tttgtctttc acggaggca                                                 79
```

<210> 52

<211> 85

<212> DNA

<213> Varicella zoster

<400> 52

```
tccatttaac gttgcatcat tttgtgttat catagaactg cgtaaacact cggcaagtaa    60
tacagataac tcgctaccgg aacgt                                          85
```

<210> 53

<211> 70

<212> DNA

<213> Adenovirus

<400> 53

```
cgccgccaac atgctctacc ctatacccgc caacgctacc aacgtgccca tatccatccc    60
ctcccgcaac                                                           70
```

<210> 54

<211> 86

<212> DNA

<213> Eubacterial 16s ribosomal RNA gene region I

<400> 54

```
tgggctacac acgtgctaca atggtcggta cagagggtcg ccaaaccgcg aggtggagct    60
```

| SEQUENCE LISTING |

```
aatctcacaa aaccgatcgt agtccg                                  86

<210>   55
<211>   86
<212>   DNA
<213>   Eubacterial 16s ribosomal RNA gene region II
<400>   55 ggcctaacac atgcaagtcg agcggatgaa aggagcttgc tcctggattc agcggcggac   60
gggtgagtaa tgcctaggaa tctgcc                                  86

<210>   56
<211>   71
<212>   DNA
<213>   Gram +ve bacterial specific portion of 16s ribosomal RNA gene
<400>   56 acgtcaaatc atcatgcccc cttatgacct gggctacaca cgtgctacaa tggacggtac   60
aaagggctgc a                                                  71

<210>   57
<211>   84
<212>   DNA
<213>   Mycobacterium tuberculosis
<400>   57 gcggaacgtg ggaccaatac ctgggttggg ccggctgctt cgggcagcaa ctcccccggg   60
ttgaagaaga aaatcacccc gtcg                                    84

<210>   58
<211>   74
<212>   DNA
<213>   Mycobacterium fortuitum
<400>   58 aacttttttg actgccagac acactattgg gctttgagac aacaggcccg tgcccctttt   60
gggggggtggc atcc                                              74

<210>   59
<211>   70
<212>   DNA
<213>   Mycobacterium chelonae
<400>   59 tggttactcg cttggtgaat atgttttata atcctgtcc accccgtgga taggtagtcg   60
gcaaaacgtc                                                    70

<210>   60
<211>   70
```

| SEQUENCE LISTING |
| --- |

<212> DNA

<213> Toxoplasma gondii

<400> 60
cccctctgct ggcgaaaagt gaaattcatg agtatctgtg caactttggt gtattcgcag    60
attggtcgcc                                                          70

<210> 61

<211> 79

<212> DNA

<213> Chlamydia trachomatis

<400> 61
aatcgtatct cgggttaatg ttgcatgatg ctttatcaaa tgacaagctt agatccgttt    60
ctcatacggt tttcctcga                                                 79

<210> 62

<211> 68

<212> DNA

<213> Fungal specific portion of 28s ribosomal RNA gene

<400> 62
gctgggactg aggactgcga cgtaagtcaa ggatgctggc ataatggtta tatgccgccc    60
gtcttgaa                                                            68

<210> 63

<211> 77

<212> DNA

<213> Propionibacterium acnes

<400> 63
tggcgaacgg gtgagtaaca cgtgagtaac ctgcccttga ctttgggata acttcaggaa    60
actggggcta ataccgg                                                  77

<210> 64

<211> 68

<212> DNA

<213> Gram -ve bacterial specific portion of gyr B gene

<400> 64
cggcggcaag ttcgacgaca acacctacaa ggtgtccggc ggcttgcacg gtgtgggcgt    60
ctcggtgg                                                            68

<210> 65

<211> 66

<212> DNA

<213> Gram -ve bacterial aconitate hydratase gene

<400> 65
ccaggtcggc ggagaagccg aggcaggcga ggtccttcag ttcgtcgcgg gtcatcgggc    60
cggtgg 66

<210> 66
<211> 64
<212> DNA
<213> Gram -ve ribonuclease 1
<400> 66
gccgccctga ccaccttcat cagcctggcc ggccgttacc tggtgctgat gccgaacaac    60
ccgc    64

<210> 67
<211> 45
<212> DNA
<213> Herpes simplex virus
<400> 67
gcaactgtgc tatccccatc acggtcatgg agtacaccga atgct    45

<210> 68
<211> 30
<212> DNA
<213> Herpes simplex virus
<400> 68
cacatcacag tcgcggcagc gtcatcggcg    30

<210> 69
<211> 37
<212> DNA
<213> Herpes simplex virus
<400> 69 tcccccctgga cgggtacggc cgcatgaacg gccgggg    37

<210> 70
<211> 31
<212> DNA
<213> Cytomegalovirus
<400> 70
aggtagaaac tgtgtgtaca gttgcgttgt g    31

<210> 71
<211> 22
<212> DNA
<213> Cytomegalovirus
<400> 71
aatacaaagc cgcagtgtcg tc    22

| SEQUENCE LISTING | |
|---|---|
| <210> 72 | |
| <211> 26 | |
| <212> DNA | |
| <213> Cytomegalovirus | |
| <400> 72 | |
| gactccaggt acaccttgac gtactg | 26 |
| <210> 73 | |
| <211> 33 | |
| <212> DNA | |
| <213> Varicella zoster | |
| <400> 73 | |
| cttaaaactc actaccagtc atttctatcc atc | 33 |
| <210> 74 | |
| <211> 36 | |
| <212> DNA | |
| <213> Varicella zoster | |
| <400> 74 | |
| ttatcataga actgcgtaaa cactcggcaa gtaata | 36 |
| <210> 75 | |
| <211> 30 | |
| <212> DNA | |
| <213> Adenovirus | |
| <400> 75 | |
| ctatacccgc caacgctacc aacgtgccca | 30 |
| <210> 76 | |
| <211> 38 | |
| <212> DNA | |
| <213> Eubacterial 16s ribosomal gene region I | |
| <400> 76 | |
| tcggtacaga gggtcgccaa accgcgaggt ggagctaa | 38 |
| <210> 77 | |
| <211> 38 | |
| <212> DNA | |
| <213> Eubacterial 16s ribosomal gene region II | |
| <400> 77 | |
| ggatgaaagg agcttgctcc tggattcagc ggcggacg | 38 |
| <210> 78 | |
| <211> 24 | |
| <212> DNA | |

SEQUENCE LISTING

<213> 16s ribosomal gene of gram-positive organism

<400> 78
gacctgggct acacacgtgc taca  24

<210> 79
<211> 42
<212> DNA
<213> *Mycobacterium tuberculosis*

<400> 79
ctgggttggg ccggctgctt cgggcagcaa ctcccccggg tt  42

<210> 80
<211> 26
<212> DNA
<213> *Mycobacterium fortuitum*

<400> 80
ggctttgaga caacaggccc gtgccc  26

<210> 81
<211> 23
<212> DNA
<213> *Mycobacterium chelonae*

<400> 81
tttataaatc ctgtccaccc cgt  23

<210> 82
<211> 27
<212> DNA
<213> *Toxoplasma gondii*

<400> 82
aaattcatga gtatctgtgc aactttg  27

<210> 83
<211> 32
<212> DNA
<213> *Chlamydia trachomatis*

<400> 83
atgatgcttt atcaaatgac aagcttagat cc  32

<210> 84
<211> 25
<212> DNA
<213> 28s ribosomal RNA gene of fungi

<400> 84

SEQUENCE LISTING

```
gtaagtcaag gatgctggca taatg                                   25

<210>      85
<211>      26
<212>      DNA
<213>      Propionibacterium acnes
<400>      85 gcttcagcgc cgtcagcgag gataac                                  26

<210>      86
<211>      30
<212>      DNA
<213>      gyrase gene of gram -ve organism
<400>      86 aacacctaca aggtgtccgg cggcttgcac                              30

<210>      87
<211>      31
<212>      DNA
<213>      aconitate hydratase gene of gram -ve organism
<400>      87 cgaggcaggc gaggtccttc agttcgtcgc g                            31

<210>      88
<211>      27
<212>      DNA
<213>      Ribonuclease gene of gram -ve organism
<400>      88 atcagcctgg ccggccgtta cctggtg                                 27
```

SEQUENCE LISTING

```
<160> NUMBER OF SEQ ID NOS: 31

<210> SEQ ID NO 1
<211> LENGTH: 1021
<212> TYPE: DNA
<213> ORGANISM: Nicotiana tabacum

<400> SEQUENCE: 1
cgcggatcca gatcttccaa caccatttac tccaagggca ctgtagtaaa aaaataatta    60
aatcattttt gaaatctaaa aaactcactt attttggacc ataaaaaaag ggccaaaaaa   120
taacttattg tggaccggag agagtaatac acttttttggt tagcgaatgc aattaattta  180
gacattgtgt tatgttccag ttaaccgctt ccctgcactt ctttcaatct atctctcgat   240
agaaaattgt gatactttgc gacttctatc agaggacttt tgttttcca tgtaacaatc    300 tgtcattttc gatggggaga tttgcacaaa taggctattt atgtgtccca atttaaattt   360
```

-continued

| | |
|---|---|
| taacccatg tcgatcagaa cttagccacg agcaccagaa gtttgatgga tatgtgactt | 420 |
| tgtcactatc cggtttacta atcaagagct attttattc aaaattggat atctagctaa | 480 |
| gtataactgg ataatttgca ttaacagatt gaatatagtg ccaaacaaga agggacaatt | 540 |
| gacttgtcac tttatgaaag atgattcaaa catgattttt tatgtactaa catatacatc | 600 |
| ctactcgaat taaagcgaca taggctcgaa gtatgcacat ttagcaatgt aaattaaatc | 660 |
| agttttgaa tcaagctaaa agcagacttg cataaggtgg gtggctggac tagaataaac | 720 |
| atcttctcta gcacagcttc ataatgtaat ttccataact gaaatcaggg tgagacaaaa | 780 |
| ttttggtact ttttcctcac actaagtcca tgtttgcaac aaattaatac atgaaaccctt | 840 |
| aatgttaccc tcagattagc ctgctactcc ccattttcct cgaaatgctc caacaaaagt | 900 |
| tagttttgca agttgttgtg tatgtcttgt gctctatata tgcccttgtg gtgcaagtgt | 960 |
| aacagtacaa catcatcact caaatcaaag tttttactta agaaattag ctaaatctag | 1020 |
| a | 1021 |

<210> SEQ ID NO 2
<211> LENGTH: 1554
<212> TYPE: DNA
<213> ORGANISM: Arabidopsis thaliana

<400> SEQUENCE: 2

| | |
|---|---|
| atgaggaaag aggagattcc agataaaagt cggactatcc cgatcgatcc gaatctgccg | 60 |
| aaatgggtct gccaaaactg tcaccactcc cttaccatcg tcggcgtcga ttcctacgcc | 120 |
| ggcaagttct tcaacgatcc ccctccgtcc gctacgcagg gctcatctat ccatggagct | 180 |
| aacagtgttc ttggttcaac acgcatggac aactcttttg ttgttttacc tcgacataag | 240 |
| cctcctcaat ctcagggcat tcctccacgt cctcgcgggg cgtcctcacc tcagcctgat | 300 |
| gctactcaat ctggaaaggc gatggaggaa tcgtttgtag ttgtctataa gtctgagcct | 360 |
| gtttctgatt ctggtggttc tcacaatctg tctcttgaag tgggccaaaa cggtcccttta | 420 |
| cattcaaata cttctggctt taatgcgact atcaatgtct taactcgtgc ttttgatatt | 480 |
| gctagaactc agacacaggt tgaacagcca ttgtgcttag aatgcatgag ggtattgtct | 540 |
| gataaacttg aaaagaagt cgaggatgtg acgagggacg tggaagcata cgaagcatgc | 600 |
| gttcagaggt tagaaggaga gacgcaagat gttcttagtg aagctgattt tctcaaggaa | 660 |
| agaagaaga ttgaggaaga agaaagaaaa cttgttgcag ctatagaaga aacagagaaa | 720 |
| caaaatgctg aagtaaacca tcaactgaag gagctagaat tcaagggaaa tcgtttttaac | 780 |
| gaacttgaag atcggtattg gcaagagttc aataattttc agtttcaatt aattgcccat | 840 |
| caggaagaga gagatgcaat cttggcaaag attgaagttt cacaagcaca tttagagtta | 900 |
| ttaaataaga caaatgtact tattgatgcc ttcccatac ggaatgatgg ggaatttggt | 960 |
| acaattaaca attttcgact tggaagactc cctgccataa aagttgagtg ggatgagatc | 1020 |
| aatgctgctt ggggccaagc ctgtcttctc ctccatacga tgtgtaacta tttccggcca | 1080 |
| aagtttcaat gtcaagttaa aatacagccg atggggagtt atcctagaat tgtagacagc | 1140 |
| aacaacgaaa cttatgagct gtttggtcct gttaacttgt tttggagcac tcggtacgat | 1200 |
| aaagccatga cactgtattt gatgtgtctt aaagactttg ctgattttgc aaattcaaag | 1260 |
| gaccaagaga caatattcc accagataat tgcctcaacc ttccatacaa gatcgaaaag | 1320 |
| gacaaagtat gggggtattc aataacacag agcttcaaca agcaagagag ttggaccaaa | 1380 |
| gcactaaagt atactctctg caacctcaaa tgggctctct actggttcgt tggaaacact | 1440 |

```
aatttccaac ctctctctgc gacggtctct ctgccttcta atatatcagc ggctggttcc    1500
ttgtacgcca agcgaggtcc tgactctagt aagccttcat gtaaaaaaac ttag          1554
```

<210> SEQ ID NO 3
<211> LENGTH: 277
<212> TYPE: DNA
<213> ORGANISM: Artificial Sequence
<220> FEATURE:
<223> OTHER INFORMATION: A synthetic oligonucleotide sequence

<400> SEQUENCE: 3

```
gagctcgaat tcccccgatc gttcaaacat ttggcaataa agtttcttaa gattgaatcc     60
tgttgccggt cttgcgatga ttatcatata atttctgttg aattacgtta agcatgtaat    120
aattaacatg taatgcatga cgttatttat gagatgggtt tttatgatta gagtcccgca    180
attatacatt taatacgcga tagaaaacaa atatagcgc gcaaactagg ataaattatc     240
gcgcgcggtg tcatctatgt tactagatcg ggaattc                             277
```

<210> SEQ ID NO 4
<211> LENGTH: 450
<212> TYPE: DNA
<213> ORGANISM: Artificial Sequence
<220> FEATURE:
<223> OTHER INFORMATION: A synthetic oligonucleotide sequence

<400> SEQUENCE: 4

```
gtcgaccatc atttgaaagg gcctcggtaa taccattgtg gaaaaagttg gtaatacgga     60
aaaagaagat tcatcatcca gaaaggtgt ggaaaagttg tggattgcgt ggaaaaagtt    120
cgatctgacc atctctagat cgtggaaaaa gttcacgtaa gcgcttacgt acatatgtgg    180
attgtggaaa aagaagacgg aggcatcggt ggaaaaagaa gcttgtacgc tgtacgctga    240
cgatagatag atacacgtgc acgcgtccac ttgacgcaca attgacgcac aatgacgcca    300
cttgacgcta cttcactata tataggaagt tcatttcatt tggaatggac acgtgttgtc    360
atttctcaac aattaccaac aacaacaaac aacaaacaac attatacaat tactatttac    420
aattacatct agataaacaa tggcttcctc                                     450
```

<210> SEQ ID NO 5
<211> LENGTH: 393
<212> TYPE: DNA
<213> ORGANISM: Arabidopsis thaliana

<400> SEQUENCE: 5

```
atgtcgaata atcaagcttt catggaattg ggatggagaa acgacgtcgg atcacttgct     60
gtgaaagatc agggcatgat gtcagaaaga gcaagaagtg atgaagatcg tctaatcaac    120
ggtctaaaat ggggctacgg ctactttgat catgatcaaa ctgataatta tcttcagatt    180
gttccagaga ttcataaaga agtagaaaat gcgaaggagg atttattggt tgttgtccct    240
gatgaacatt ctgaaactga tgatcatcat catattaaag atttttcaga gagatcagat    300
catcgatttt atctgagaaa caaacatgag aaccccaaaa aacgtcgtat ccaggtctta    360
agtagtgatg atgaatcgga ggagtttaca aga                                 393
```

<210> SEQ ID NO 6
<211> LENGTH: 603
<212> TYPE: DNA
<213> ORGANISM: Arabidopsis thaliana

```
<400> SEQUENCE: 6
atgactgatc aaggattgga agggagtaat ccagttgatc ttagcaagca tccttcaggg    60
attgttccta ctcttcaaaa cattgtctcc acggtgaact tagactgcaa gctagatctt   120
aaagccatag ctttgcaggc tcggaatgct gaatataatc ccaagcgttt tgctgcggtg   180
ataatgagga tcagagaacc gaagactaca gcattaatat tcgcctcagg gaaaatggtc   240
tgtactggag ctaagagcga ggacttttcg aagatggctg ctagaaagta tgctaggatt   300
gtgcagaaat tgggattccc tgcaaaattc aaggatttca agattcagaa tattgtaggt   360
tcttgtgatg tcaaattccc tataagactt gaaggtcttg cttactctca cgctgctttc   420
tcaagttatg agcccgagct cttcccaggg ctgttttata ggatgaaagt cccaaaaatc   480
acccttgtaa tctttgtctc tgggaagatc gtaataacag gagccaagat gagagatgag   540
acctacaaag cctttgagaa atatacccc gtgctctcgg aattcagaaa gatacagcaa   600
tag                                                                 603

<210> SEQ ID NO 7
<211> LENGTH: 1952
<212> TYPE: DNA
<213> ORGANISM: Arabidopsis thaliana

<400> SEQUENCE: 7
tctagacata acggtgagag ttaatattaa aatttcaggc gagaaaatg atacttgaaa     60 aatattatga tcgttttgga tattccttac atcgagtgaa tgttggtttg attcatcttc   120
caagtgttct gcaaacgtat attaaaggtt tattaactgg taagagatta accgggtttt   180
ggttcagcat ataccatgat tgactaactg atcaaatagt cttacttat tatataaaga    240 cgatactatt ggtcatgcta caaaatcaag tcataccata tcctgagaat gaatgtggag   300
aatcgttata aggcataagt gtgggtattg atcgtggtac gaacaaccgc cttggcatca   360
acattagcca cgatatccaa catttgaagc attgcctatg gcgagtgttt ggttggtttt   420
gaaactgatg atgataacca gaacgagaaa tgtcttgtga agtataatgt tccgatgaat   480
tgggattata ataatgtgta gacattgtag gttggttttg atgatgataa gtaatcattg   540
gagaattgtc taacacatgc actggagaat tattgactct accacgttct ctttgatatt   600
cctcgatttt cctcgtgatt tcatcagcct ctccgaaaaa gtaattgtat ccactagaac   660
tttgggaatc tcccatctaa tttatgtatt agagaagtta taatattttg gggaaataga   720
ttttctctac tgattttgtt gtgtgacatt atattttta agtacatgt ttctgtttcg     780 ttatattgtt gtcgtggttg agtctttatt agagcatgta aatatgttta tgaaataagc   840
gagaaaggaa ttaattaaac gtatcgagtg ataaatgctt taatggattc gagatttagt   900
attcttaaat ttttgtttca ttatcattga ttataaaact aagttatgtt gatctcaaat   960
ccttaattat gttctcctaa gaagagtaca agtggtggga acgaaagatg agtaaaatac  1020
taaaaatctt ttctcaaaag tcaaatcgca ttagttaaca aaaacaaacc atgtgttacc  1080
gtcaaatcaa tgtgtttaaa agatgttaac cactaatcaa gcatttacgt gtaaccggat  1140
caaccggatt tgggttttga atatgttgtg gagatgtata taaatgataa attaattgaa  1200
tatcttaatt aatctgtgaa agaaactaca tcacacactt tgttatttcc cctagctttt  1260
agttttttta tcatgcaaaa cttatgaagt aactagatca agatcacaaa aaaaaagcat  1320
cacttcactt catgacctaa ttattctcga agcccaaaac tatttacata cacttttatt  1380
ctataaatat agatgatgga attcaccaat ccaaaagtga ataaaaaaca caagtacaaa  1440
```

```
caatatagta tctaattaga atggtatctc taaagtccct tgctgctatt ctcgttgcca    1500
tgtttcttgc caccggacct acggttctag cccagcagtg cagagacgaa ctgagcaatg    1560
tgcaggtgtg cgcgccgctg cttctgcccg gtgcggtcaa tcctgccgcg aactcaaatt    1620
gctgcgctgc cctccaagca actaacaaag attgtctatg taaccgtctt cgagcagcca    1680
ccacacttac ctctctttgt aacctcccct cttttgattg tggtaagatg atccatcgat    1740
taaaaccttt tttactagat ttttataaat tattccatca atagtgtttg ttttatattt    1800
gttctcatga ttttttggac ttatgttttg tgaactgtgc aggcataagt gcctagttga    1860
acaacattca gttccgagga tttggggagt ttggtctgca acgacaaga cgaataaaat    1920 aaaataatga gaaatacact atttagtgtt tt    1952

<210> SEQ ID NO 8
<211> LENGTH: 2007
<212> TYPE: DNA
<213> ORGANISM: Arabidopsis thaliana

<400> SEQUENCE: 8
atggaagaga tttcgacgga tccggttgtt ccagcggtga aacctgaccc gagaacatct      60
tcagttggtg aaggtgctaa tcgtcatgaa atgacgacg gaggaagcgg cggttctgag     120
attggagcac cggatctgga taagacttg ctttgtccga tttgtatgca gattattaaa     180
gatgctttcc tcacggcttg tggtcatagt ttctgctata tgtgtatcat cacacatctt     240
aggaacaaga gtgattgtcc ctgttgtagc aacacctca ccaataatca gctttaccct     300
aatttcttgc tcgataagct attgaagaaa acttcagctc ggcatgtgtc aaaaactgca     360
tcgcccttgg atcagtttcg ggaagcacta caaggggtt gtgatgtgtc aattaaggag     420
gttgataatc ttctgacact tcttgcggaa aggaagagaa aaatggaaca ggaagaagct     480
gagaggaaca tgcagatact tttggacttt ttgcattgtc taaggaagca aaaagttgat     540
gaactaaatg aggtgcaaac tgatctccag tatattaaag aagatataaa tgccgttgag     600
agacatagaa tagatttata ccgagctagg gacagatatt ctgtaaagtt gcggatgctc     660
ggagatgatc caagcacaag aaatgcatgg ccacatgaga agaaccagat tggttttcaac     720 tccaattctc tcagcataag aggaggaaat tttgtaggca attatcaaaa caaaaaggta     780
gaggggaagg cacaaggaag ctctcatggg ctaccaaaga aggatgcgct gagtgggtca     840
gattcgcaaa gtttgaatca gtcaactgtc tcaatggcta gaaagaaacg gattcatgct     900
cagttcaatg atttacaaga atgttacctc caaaagcggc gtcagttggc agaccaacca     960
aatagtaaac aagaaaatga taagagtgta gtacggaggg aaggctatag caacggcctt    1020
gcagattttc aatctgtgtt gactaccttc actcgctaca gtcgtctaag agttatagca    1080
gaaatccggc atggggatat atttcattca gccaacattg tatcaagcat agagtttgat    1140
cgtgatgatg agctgtttgc cactgctggt gtttctagat gtataaaggt ttttgacttc    1200
tcttcggttg taaatgaacc agcagatatg cagtgtccga ttgtggagat gtcaactcgg    1260
tctaaactta gttgcttgag ttggaataag catgaaaaaa atcacatagc aagcagtgat    1320
tatgaaggaa tagtaacagt gtgggatgta actactaggc agagtcttat ggagtatgaa    1380
gagcacgaaa acgtgcctg gagtgttgac ttttcacgaa cagaaccatc aatgcttgta    1440
tctggtagtg acgactgcaa ggttaaagtt tggtgcacga ggcaggaagc aagtgtgatt    1500
aatattgata tgaaagcaaa catatgttgt gtcaagtaca atcctggctc aagcaactac    1560
```

```
attgcggtcg gatcagctga tcatcacatc cattattacg atctaagaaa cataagccaa   1620
ccacttcatg tcttcagtgg acacaagaaa gcagtttcct atgttaaatt tttgtccaac   1680
aacgagctcg cttctgcgtc cacagatagc acactacgct tatgggatgt caaagacaac   1740
ttgccagttc gaacattcag aggacatact aacgagaaga actttgtggg tctcacagtg   1800
aacagcgagt atctcgcctg tggaagcgag acaaacgaag tatatgtata tcacaaggaa   1860
atcacgagac ccgtgacatc gcacagattt ggatcgccag acatggacga tgcagaggaa   1920
gaggcaggtt cctactttat tagtgcggtt tgctggaaga gtgatagtcc cacgatgttg   1980
actgcgaata gtcaaggaac catcaaa                                       2007
```

```
<210> SEQ ID NO 9
<211> LENGTH: 307
<212> TYPE: DNA
<213> ORGANISM: Artificial Sequence
<220> FEATURE:
<223> OTHER INFORMATION: A synthetic oligonucleotide sequence

<400> SEQUENCE: 9
gatcatgagc ggagaattaa gggagtcacg ttatgacccc cgccgatgac gcgggacaag     60
ccgttttacg tttggaactg acagaaccgc aacgttgaag gagccactca gccgcgggtt   120
tctggagttt aatgagctaa gcacatacgt cagaaaccat tattgcgcgt tcaaaagtcg   180
cctaaggtca ctatcagcta gcaaatattt cttgtcaaaa atgctccact gacgttccat   240
aaattcccct cggtatccaa ttagagtctc atattcactc tcaatccaaa taatctgcac   300
cggatct                                                             307
```

```
<210> SEQ ID NO 10
<211> LENGTH: 24
<212> TYPE: DNA
<213> ORGANISM: Artificial Sequence
<220> FEATURE:
<223> OTHER INFORMATION: A synthetic primer

<400> SEQUENCE: 10
ttcgcggccg ataaggcagc gaag                                           24
```

```
<210> SEQ ID NO 11
<211> LENGTH: 24
<212> TYPE: DNA
<213> ORGANISM: Artificial Sequence
<220> FEATURE:
<223> OTHER INFORMATION: A synthetic primer

<400> SEQUENCE: 11
ttcttgctcg ataagctatt gaag                                           24
```

```
<210> SEQ ID NO 12
<211> LENGTH: 46
<212> TYPE: DNA
<213> ORGANISM: Artificial Sequence
<220> FEATURE:
<223> OTHER INFORMATION: A synthetic primer

<400> SEQUENCE: 12
gctttaccct aatttcgcgg cccgataagc tattgaagaa aacttc                   46
```

```
<210> SEQ ID NO 13
<211> LENGTH: 44
<212> TYPE: DNA
<213> ORGANISM: Artificial Sequence
```

```
<220> FEATURE:
<223> OTHER INFORMATION: A synthetic primer

<400> SEQUENCE: 13
gttttcttca atagcttatc ggccgcgaaa ttagggtaaa gctg            44

<210> SEQ ID NO 14
<211> LENGTH: 44
<212> TYPE: DNA
<213> ORGANISM: Artificial Sequence
<220> FEATURE:
<223> OTHER INFORMATION: A synthetic primer

<400> SEQUENCE: 14
taatttcttg ctcgataagg cagcgaagaa aacttcagct cggc            44

<210> SEQ ID NO 15
<211> LENGTH: 44
<212> TYPE: DNA
<213> ORGANISM: Artificial Sequence
<220> FEATURE:
<223> OTHER INFORMATION: A synthetic primer

<400> SEQUENCE: 15
cgagctgaag ttttcttcgc tgccttatcg agcaagaaat tagg            44

<210> SEQ ID NO 16
<211> LENGTH: 22
<212> TYPE: DNA
<213> ORGANISM: Artificial Sequence
<220> FEATURE:
<223> OTHER INFORMATION: A synthetic primer

<400> SEQUENCE: 16
aagggcctcg gtaataccat tg                                    22

<210> SEQ ID NO 17
<211> LENGTH: 27
<212> TYPE: DNA
<213> ORGANISM: Artificial Sequence
<220> FEATURE:
<223> OTHER INFORMATION: A synthetic primer

<400> SEQUENCE: 17
ccatcgatct agtaacatag atgacac                               27

<210> SEQ ID NO 18
<211> LENGTH: 34
<212> TYPE: DNA
<213> ORGANISM: Artificial Sequence
<220> FEATURE:
<223> OTHER INFORMATION: A synthetic primer

<400> SEQUENCE: 18
acgcgtcgac tctagacata acggtgagag ttaa                       34

<210> SEQ ID NO 19
<211> LENGTH: 30
<212> TYPE: DNA
<213> ORGANISM: Artificial Sequence
<220> FEATURE:
<223> OTHER INFORMATION: A synthetic primer

<400> SEQUENCE: 19
cgagctctca cgcagcgagt accagaactt                            30
```

<210> SEQ ID NO 20
<211> LENGTH: 19
<212> TYPE: DNA
<213> ORGANISM: Artificial Sequence
<220> FEATURE:
<223> OTHER INFORMATION: A synthetic primer

<400> SEQUENCE: 20
aagcggcggt tctgagatt                                                19

<210> SEQ ID NO 21
<211> LENGTH: 20
<212> TYPE: DNA
<213> ORGANISM: Artificial Sequence
<220> FEATURE:
<223> OTHER INFORMATION: A synthetic primer

<400> SEQUENCE: 21
accacaagcc gtgaggaaag                                               20

<210> SEQ ID NO 22
<211> LENGTH: 18
<212> TYPE: DNA
<213> ORGANISM: Artificial Sequence
<220> FEATURE:
<223> OTHER INFORMATION: A synthetic primer

<400> SEQUENCE: 22
agggcattcc tccacgtc                                                 18

<210> SEQ ID NO 23
<211> LENGTH: 25
<212> TYPE: DNA
<213> ORGANISM: Artificial Sequence
<220> FEATURE:
<223> OTHER INFORMATION: A synthetic primer

<400> SEQUENCE: 23
aagagacaga ttgtgagaac cacca                                         25

<210> SEQ ID NO 24
<211> LENGTH: 19
<212> TYPE: DNA
<213> ORGANISM: Artificial Sequence
<220> FEATURE:
<223> OTHER INFORMATION: A synthetic primer

<400> SEQUENCE: 24
ccacggagac ggaggacaa                                                19

<210> SEQ ID NO 25
<211> LENGTH: 20
<212> TYPE: DNA
<213> ORGANISM: Artificial Sequence
<220> FEATURE:
<223> OTHER INFORMATION: A synthetic primer

<400> SEQUENCE: 25
gaagcagctc gaggatggaa                                               20

<210> SEQ ID NO 26
<211> LENGTH: 32
<212> TYPE: DNA
<213> ORGANISM: Artificial Sequence
<220> FEATURE:
<223> OTHER INFORMATION: A synthetic primer

```
<400> SEQUENCE: 26
ccgctcgaga tggaagagat ttcgacggat cc                                    32

<210> SEQ ID NO 27
<211> LENGTH: 30
<212> TYPE: DNA
<213> ORGANISM: Artificial Sequence
<220> FEATURE:
<223> OTHER INFORMATION: A synthetic primer

<400> SEQUENCE: 27
cgagctctca cgcagcgagt accagaactt                                       30

<210> SEQ ID NO 28
<211> LENGTH: 33
<212> TYPE: DNA
<213> ORGANISM: Artificial Sequence
<220> FEATURE:
<223> OTHER INFORMATION: A synthetic primer

<400> SEQUENCE: 28
ccatcgatat gtcgaataat caagctttca tgg                                   33

<210> SEQ ID NO 29
<211> LENGTH: 32
<212> TYPE: DNA
<213> ORGANISM: Artificial Sequence
<220> FEATURE:
<223> OTHER INFORMATION: A synthetic primer

<400> SEQUENCE: 29
ccatcgattc ttgtaaactc ctccgattca tc                                    32

<210> SEQ ID NO 30
<211> LENGTH: 38
<212> TYPE: DNA
<213> ORGANISM: Artificial Sequence
<220> FEATURE:
<223> OTHER INFORMATION: A synthetic primer

<400> SEQUENCE: 30
cgcggatcca gatcttccaa caccatttac tccaaggg                              38

<210> SEQ ID NO 31
<211> LENGTH: 35
<212> TYPE: DNA
<213> ORGANISM: Artificial Sequence
<220> FEATURE:
<223> OTHER INFORMATION: A synthetic primer

<400> SEQUENCE: 31
cgtcgagctc ctaagttttt ttacatgaag gctta                                 35
```

We claim:

1. A MS DNA construct comprising:
   a. a first expression cassette comprising a first tapetum specific promoter operably linked to a desired gene of interest, expression of which leads to male sterility in plants, and a terminator; and wherein said desired gene of interest is AtBECLIN1 comprising SEQ ID NO: 2; and
   b. a second regulatory cassette comprising a second promoter operably linked to a fragment encoding a fusion peptide of i) N-terminal fragment of a transcription factor selected from the group consisting of HY5, HYH, and HFR1 and ii) TBPm3 encoded by SEQ ID NO: 6, and a terminator.

2. A ES DNA construct comprising:
   a. a first expression cassette comprising a first tapetum specific promoter operably linked to a gene of interest, and a terminator; and
   b. a second regulatory cassette comprising a second promoter operably linked to a fragment encoding a fusion peptide of i) N-terminal fragment of a transcription factor selected from the group consisting of HY5, HYH, and HFR1 and ii) TBPm3 encoded by SEQ ID NO: 6, and a terminator.

3. A RS DNA construct comprising an expression cassette comprising a tapetum specific promoter operably linked to a gene encoding a gene product that is a repressor of light signaling, and a terminator wherein said gene or gene product inactivates a transcription factor selected from the group consisting of HY5, HYH, and HFR1, wherein the gene comprises SEQ ID NO:8.

4. A reversible expression system for modulating male sterility in plants, said system comprising:
   a. a first component consisting of:
      i. a first expression cassette comprising: a first tapetum specific promoter operably linked to a desired gene of interest, expression of which causes male sterility in plants, and a terminator; and wherein said desired gene of interest is AtBECLIN1 comprising SEQ ID NO: 2; and
      ii. a second regulatory cassette comprising: a second promoter operably linked to a fragment encoding a fusion peptide of i) N-terminal fragment of a transcription factor selected from the group consisting of HY5, HYH, and HFR1 and ii) TBPm3 encoded by SEQ ID NO: 6, and a terminator; and
   b. a second component consisting of an expression cassette comprising: a second tapetum specific promoter operably linked to a gene, and a terminator.

5. A reversible expression system for modulating transgene expression in plants, said system comprising:
   a. a first component consisting of:
      i. a first expression cassette comprising: a first tapetum specific promoter operably linked to a gene of interest comprising AtBECLIN1 comprising SEQ ID NO: 2, and a terminator; and
      ii. a second regulatory cassette comprising: a second promoter operably linked to a fragment encoding a fusion peptide of i) N-terminal fragment of a transcription factor selected from the group consisting of HY5, HYH, and HFR1 and ii) TBPm3 encoded by SEQ ID NO: 6, and a terminator; and
   b. a second component consisting of an expression cassette comprising: a second tapetum specific promoter operably linked to a gene encoding a gene product that inactivates a transcription factor selected from the group consisting of HY5 and HYH, and a terminator.

6. The reversible expression system as claimed in claim 5, wherein said AtBECLIN1 consists of SEQ ID NO: 2.

7. The ES DNA construct as claimed in claim 2 or the system as claimed in claim 5, wherein said gene of interest is selected from the group consisting of gusA, GFP, YFP, LUX.

8. The MS DNA construct as claimed in claim 1 or the system as claimed in claim 4, wherein said first tapetum specific promoter is tapetum specific promoter TA29 having SEQ ID NO: 1.

9. The RS DNA construct as claimed in claim 3 or the system as claimed in claim 4, wherein said tapetum specific promoter is tapetum specific promoter having SEQ ID NO: 7.

10. The MS DNA construct as claimed in claim 1 or the system as claimed in claim 4, wherein said second promoter is constitutive or tissue specific.

11. The MS DNA construct or system as claimed in claim 10, wherein said second promoter is a constitutive promoter having SEQ ID NO: 4.

12. The MS DNA construct as claimed in claim 1, or the ES DNA construct as claimed in claim 2, or the system as claimed in claim 4, wherein said N-terminal fragment of a transcription factor consists of HFR1 encoded by SEQ ID NO:5.

13. The MS DNA construct as claimed in claim 1, or the ES DNA construct as claimed in claim 2, or the RS DNA construct as claimed in claim 3, or the system as claimed in claim 4, wherein said terminator is Nos terminator having SEQ ID NO: 3.

14. The RS DNA construct as claimed in claim 3 or the system as claimed in claim 4, wherein said gene is a mutant COP1 comprising SEQ ID NO: 8.

15. A DNA vector comprising a MS DNA construct as claimed in claim 1, or a ES DNA construct as claimed in claim 2, or a RS DNA construct as claimed in claim 3.

16. A recombinant host cell comprising a MS DNA construct as claimed in claim 1, or a ES DNA construct as claimed in claim 2, or a RS DNA construct as claimed in claim 3 or a DNA vector of claim 15.

17. A transgenic plant or parts thereof, including seeds comprising a MS DNA construct as claimed in claim 1, wherein the transgenic plant is male sterile.

18. A method of obtaining a transgenic plant of claim 17, said method comprising:
   a. obtaining a MS DNA construct as claimed in claim 1; or
   b. obtaining a recombinant host cell comprising said MS DNA construct;
   c. transforming plant cells with said MS DNA construct or recombinant host cells to obtain transformed cells; and
   d. selecting and regenerating transformed cells to obtain said transgenic plant or parts thereof, including seeds of claim 17, wherein said transgenic plant is male sterile.

19. A transgenic plant or parts thereof, including seeds comprising a RS DNA construct of claim 3.

20. A method of obtaining a transgenic plant of claim 19, said method comprising:
   a. obtaining a RS DNA construct as claimed in claim 3; or
   b. obtaining a recombinant host cell comprising said RS DNA construct;
   c. transforming plant cells with said RS DNA construct or recombinant host cells to obtain transformed cells; and
   d. selecting and regenerating transformed cells to obtain said transgenic plant or parts thereof, including seeds.

21. A hybrid plant or parts thereof, including seeds, comprising a MS DNA construct of claim 1 and a RS DNA construct of claim 3.

22. A method of obtaining a hybrid plant or part thereof, including seeds, said method comprising:
   a. obtaining a female transgenic plant having the MS DNA construct as claimed in claim 1, wherein said plant is male sterile;
   b. obtaining a male transgenic plant having the RS DNA construct as claimed in claim 3, wherein said plant is capable of restoring male fertility;
   c. crossing said female and male plant;
   d. obtaining hybrid seeds from said female plant of step (c) which comprises MS DNA construct of claim 1 and RS DNA construct of claim 3, wherein in said seeds male fertility is restored; and optionally
   e. developing said hybrid seeds into plants which comprise MS DNA construct of claim 1 and RS DNA construct of claim 3, wherein in said plants male fertility is restored.

23. A transgenic plant or parts thereof, including seeds comprising a ES DNA construct of claim 2, wherein said plant is capable of expression of a gene of interest.

24. A method of obtaining transgenic plant, said method comprising:
   a. obtaining a ES DNA construct as claimed in claim 2; or
   b. obtaining a recombinant host cell comprising said ES DNA construct;
   c. transforming plant cells with said ES DNA construct or recombinant host cells to obtain transformed cells; and
   d. selecting and regenerating transformed cells to obtain a transgenic plant, wherein said plant express gene of interest.

25. A method of obtaining transgenic plant, said method comprising:
   a. obtaining a RS DNA construct as claimed in claim 3; or
   b. obtaining a recombinant host cell comprising said RS DNA construct;
   c. transforming plant cells with said RS DNA construct or recombinant host cells to obtain transformed cells; and
   d. selecting and regenerating transformed cells to obtain a transgenic plant, wherein said plant is capable of inhibiting expression of a gene of interest.

26. The transgenic plant as claimed in claim 23, wherein said gene of interest is selected from the group consisting of gusA, GFP, YFP, LUX, nptI, and nptII genes.

27. A method of switching off expression of a gene of interest in a F1 population of plants or parts thereof, including seeds, said method comprising:
   a. obtaining a female transgenic plant of claim 17;
   b. obtaining a male transgenic plant of claim 25;
   c. crossing said female and male plant; and
   d. obtaining hybrid seeds from said female plant of step (c), wherein said hybrid seeds comprise ES DNA construct of claim 2 and RS DNA construct of claim 3, wherein the RS DNA construct inhibits the expression of gene of interest selected from the group consisting of gusA, GFP, YFP and LUX, of the ES DNA construct.

28. A method of switching off expression of a gene of interest in a F1 population of plants or parts thereof, including seeds as claimed in claim 27, wherein said method further comprises growing hybrid seeds into hybrid plants which comprise ES DNA construct of claim 2 and RS DNA construct of claim 3 and does not express said gene of interest.

* * * * *